US012171877B2

(12) United States Patent
Freeman et al.

(10) Patent No.: US 12,171,877 B2
(45) Date of Patent: Dec. 24, 2024

(54) MATERIALS AND METHODS FOR DELIVERING COMPOSITIONS TO SELECTED TISSUES

(71) Applicant: The Regents of the University of California, Oakland, CA (US)

(72) Inventors: William R. Freeman, Del Mar, CA (US); Michael J. Sailor, La Jolla, CA (US); Lingyun Cheng, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 533 days.

(21) Appl. No.: 16/270,259

(22) Filed: Feb. 7, 2019

(65) Prior Publication Data
US 2020/0009053 A1 Jan. 9, 2020

Related U.S. Application Data

(63) Continuation of application No. 12/668,349, filed as application No. PCT/US2008/069474 on Jul. 9, 2008, now abandoned.

(60) Provisional application No. 60/948,816, filed on Jul. 10, 2007.

(51) Int. Cl.
| | |
|---|---|
| *A61K 9/14* | (2006.01) |
| *A61K 9/00* | (2006.01) |
| *A61K 9/51* | (2006.01) |
| *A61K 9/70* | (2006.01) |
| *A61K 31/573* | (2006.01) |
| *A61K 31/7088* | (2006.01) |
| *A61K 38/48* | (2006.01) |
| *A61K 39/00* | (2006.01) |
| *A61K 39/395* | (2006.01) |
| *A61K 39/44* | (2006.01) |
| *C25F 3/12* | (2006.01) |

(52) U.S. Cl.
CPC ............ *A61K 9/143* (2013.01); *A61K 9/0019* (2013.01); *A61K 9/0051* (2013.01); *A61K 9/14* (2013.01); *A61K 9/5115* (2013.01); *A61K 9/7007* (2013.01); *A61K 31/573* (2013.01); *A61K 31/7088* (2013.01); *A61K 38/482* (2013.01); *A61K 39/395* (2013.01); *A61K 39/44* (2013.01); *C25F 3/12* (2013.01); *A61K 2039/505* (2013.01); *A61K 2039/54* (2013.01); *C12Y 304/21073* (2013.01)

(58) Field of Classification Search
None
See application file for complete search history.

(56) References Cited

U.S. PATENT DOCUMENTS

| | | | |
|---|---|---|---|
| 2,674,743 | A | 4/1954 | Gaiser et al. |
| 5,091,061 | A | 2/1992 | Kotah et al. |
| 5,242,950 | A | 9/1993 | Hastings |
| 6,322,895 | B1 | 11/2001 | Winget et al. |
| 6,666,214 | B2 | 12/2003 | Canham |
| 6,770,480 | B1 | 8/2004 | Canham |
| 6,929,950 | B2 | 8/2005 | Canham et al. |
| 7,332,339 | B2 | 2/2008 | Canham |
| 7,763,277 | B1 | 7/2010 | Canham et al. |
| 8,088,401 | B2 | 1/2012 | Saffie et al. |
| 8,097,236 | B2 | 1/2012 | Aston et al. |
| 8,147,864 | B2 | 4/2012 | Canham et al. |
| 8,293,630 | B2 | 10/2012 | Dunkley et al. |
| 8,303,975 | B2 | 11/2012 | Canham et al. |
| 8,313,761 | B2 | 11/2012 | Canham et al. |
| 8,318,194 | B2 | 11/2012 | Canham et al. |
| 8,361,491 | B2 | 1/2013 | Canham et al. |
| 2003/0060878 | A1 | 3/2003 | Shadduck et al. |
| 2003/0146109 | A1 | 8/2003 | Sailor et al. |
| 2003/0180294 | A1 | 9/2003 | DeVries |
| 2004/0052867 | A1 | 3/2004 | Canham |
| 2004/0101822 | A1 | 5/2004 | Wiesner et al. |
| 2004/0244889 | A1 | 12/2004 | Sailor et al. |
| 2005/0009374 | A1 | 1/2005 | Gao et al. |
| 2005/0042764 | A1 | 2/2005 | Sailor et al. |
| 2005/0101026 | A1 | 5/2005 | Sailor et al. |
| 2005/0181049 | A1 | 8/2005 | Dong et al. |
| 2006/0024350 | A1 | 2/2006 | Varner |
| 2006/0154069 | A1 | 7/2006 | Lin et al. |
| 2006/0236436 | A1 | 10/2006 | Li et al. |
| 2006/0255008 | A1 | 11/2006 | Link et al. |
| 2007/0154522 | A1 | 7/2007 | Chow et al. |
| 2008/0102306 | A1 | 5/2008 | Kirtland et al. |
| 2009/0208556 | A1 | 8/2009 | California |
| 2013/0064965 | A1 | 3/2013 | Canham et al. |

FOREIGN PATENT DOCUMENTS

| | | |
|---|---|---|
| AU | 753542 | 2/2000 |
| CA | 2228426 | 2/1997 |
| CA | 2368679 | 11/2000 |
| CA | 2228426 C | 2/2008 |

(Continued)

OTHER PUBLICATIONS

Rosenfeld (N Engl J Med, 355 (2006), pp. 1419-1431).*

(Continued)

*Primary Examiner* — Nicole P Babson

(74) *Attorney, Agent, or Firm* — Gavrilovich, Dodd & Lindsey LLP

(57) ABSTRACT

This invention relates to devices, systems and methods for delivering preprogrammed quantities of an active ingredient to a biological system over time without the need for external power or electronics.

11 Claims, 11 Drawing Sheets

(56) References Cited

FOREIGN PATENT DOCUMENTS

| | | |
|---|---|---|
| CA | 2328996 C | 12/2012 |
| CN | 99809028.X | 8/2001 |
| CN | 00809693.7 | 8/2002 |
| EP | 842113 A | 5/1998 |
| EP | 1407764 A1 | 4/2004 |
| EP | 1071398 B1 | 5/2004 |
| EP | 1776949 A2 | 4/2007 |
| EP | 2269574 A2 | 1/2011 |
| GB | 9909996.2 | 5/1999 |
| HK | 02100735.8 | 4/2002 |
| KR | 1020017013948 | 11/2000 |
| KR | 10200470143 | 8/2004 |
| KR | 20017001028 | 10/2006 |
| NZ | 509142 | 1/2004 |
| NZ | 515189 | 5/2004 |
| WO | 1997/006101 | 2/1997 |
| WO | 2000/066190 | 11/2000 |
| WO | 01/76564 A1 | 10/2001 |
| WO | 02/15863 A1 | 2/2002 |
| WO | 03/011251 A1 | 2/2003 |
| WO | 200410890 A1 | 2/2004 |
| WO | 2004/071949 | 8/2004 |
| WO | 2005/034725 | 4/2005 |
| WO | 2006/050221 A2 | 5/2006 |
| WO | 2007034196 A2 | 3/2007 |
| WO | 2009/009563 A9 | 1/2009 |

OTHER PUBLICATIONS

Office Action, Application No. KR10-2017-7019173, Korean Patent Office, Sep. 19, 2017.
Anglin, Emily J., "Porous silicon in drug delivery devices and materials," Advanced Drug Delivery Reviews 60:1266-1277 (2008).
Baharlou, Simin. International Preliminary Report on Patentability and Written Opinion. International Application No. PCT/US2006/069474. Date of Issuance of this report: Jan. 12, 2010.
Campbell, Jenna. "Development of porous silicon microfilters." Undergraduate Thesis. Georgia Institute of Technology (2007).
Cheng, L. et al., "Intravitreal properties of porous silicon photonic crystals: A potential self-reporting intraocular drug-delivery vehicle," Br. J. Ophthalmol, 2008, vol. 92, pp. 705-711.
Chhablani et al., "Oxidized Porous Silicon Particles Covalently Grafted with Daunorubicin as a Sustained Intraocular Drug Delivery System," Invest. Ophthal. & Visual Sci., Feb. 2013, vol. 54, No. 2, pp. 1268-1279.
Cui, H. et al., "Origin of Self-Limiting Oxidation of Si Nanowires," American Chemical Society, Nano Letters, 2008, vol. 8, No. 9, pp. 2731-2737.
Deal, B.E., et al., "General Relationship for the Thermal Oxidation of Silicon," Journal of Applied Physics, 1965, vol. 36, No. 12, pp. 3770-3778.
Doremus et al., "Diffusion of Reactive Molecules in Solids and Melts," John Wiley & Sons: New York, 2002, p. 164.
Doremus, R.H., "Oxidation of Silicon by Water and Oxygen and Diffusion in Fused Silica," Journal of Physical Chemistry, 1976, vol. 80, No. 16, pp. 1773-1775.
Froner, Elena et al., "Luminescence of porous silicon derived nanocrystals dispersed in water: dependence on initial porous silicon oxidation," J. of Nanoparticle Research 8:1071-1074 (2006).
Ghali, Isis A., International Search Report and Written Opinion, Date of Mailing of Report: May 23, 2007, International Application No. PCT/US05/39177, 6 pages.
Han, Jung Hee. International Search Report and Written Opinion. International Application No. PCT/US2008/069474. Date of mailing of the search report: Jun. 22, 2009.
Harvey, Michael. Examination Report. New Zealand Application No. 583120. Date of Report: Nov. 12, 2010.
Hoshino, Syoei, Office Action, Application No. 2010-516212, Japanese Patent Office, Date of Mailing: Jun. 9, 2015.
Jarvis, K. et al., "Surface chemical modification to control molecular interactions with porous silicon," Journal of Colloid and Interface Science, 2011, vol. 363, pp. 327-333.
Khalilov, U. et al., "Self-Limiting Oxidation in Small-Diameter Si Nanowires," Chemistry of Materials, 2012, vol. 24, pp. 2141-2147.
Li, Y. Y. et al., "Polymer replicas of photonic porous silicon for sensing and drug delivery applications," Science, 2003, pp. 2045-2047, vol. 299.
Liu, Huiying. The First Office Action. Chinese Application No. 200880106417.9. Date of Mailing Mar. 9, 2011.
Moon, Sun Heup. International Search Report and Written Opinion. International Application No. PCT/US2010/024848. Date of Mailing: Sep. 16, 2010.
Nieto et al., "Ocular silicon distribution an dclearance following intravitreal injetion of porous silicon microparticles," Exp. Eye Res., 2013, vol. 116, pp. 161-168.
Pap et al., "Thermal oxidation of porous silicon: Study on Reaction Kinetics," J.Phys. Chem. B, 2004, 108, pp. 12744-12747.
Pap et al., "Thermal oxidation of porous silicon: Study on structure," Appl. Physics Lett., 2005, vol. 86, pp. 041501.
Sindel, Ulrike, Communication Pursuant to Article 94(3) EPC, European Patent Application No. 08826216.7, Jun. 29, 2016.
Sweryda-Krawiec, Beata et al., "A comparison of porous silicon and silicon nanocrystallite photoluminescence quenching with amines," J. Physic. Chem. 100:13776-13780 (1996).
Williams, E.L., "Diffusion of Oxygen in Fused Silica," J. Am. Ceram. Soc., vol. 48, No. 4, pp. 190-194.
Wittmann-Regis, Agnes, International Preliminary Report on Patentability and Written Opinion, Date of Issuance of Report: Jun. 26, 2007, International Application No. PCT/US05/39177, 4 pages.
Wu et al., "Sutability of porous silicon microparticles for long-term delivery of redox-active therapeutics," Chem. Commun. 2011, vol. 47, pp. 5699-5701.

\* cited by examiner

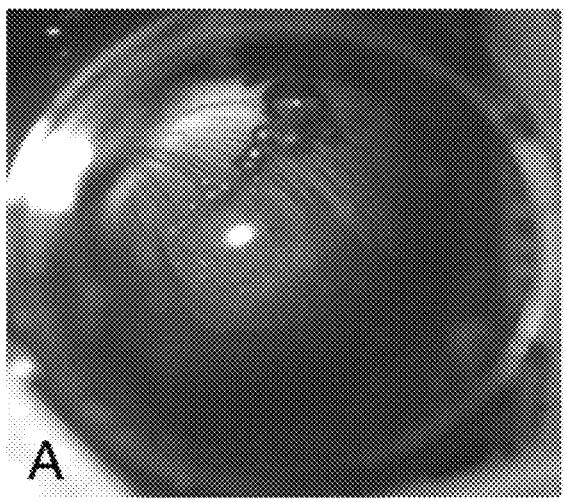 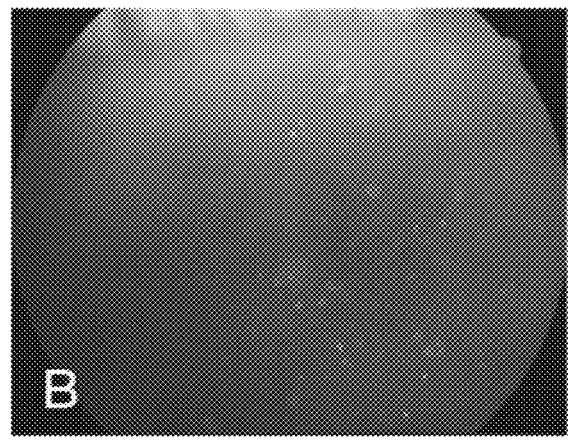
FIG. 7A  FIG. 7B
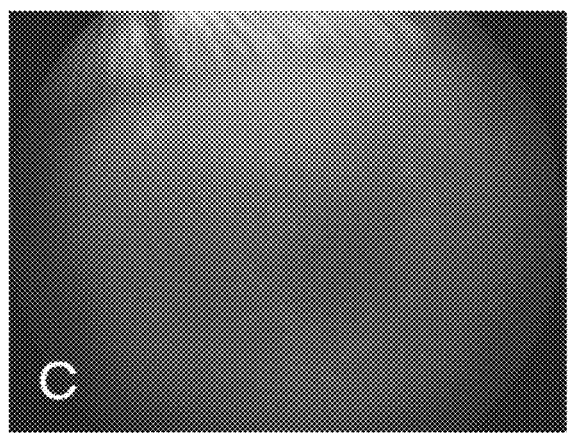 
FIG. 7C  FIG. 7D
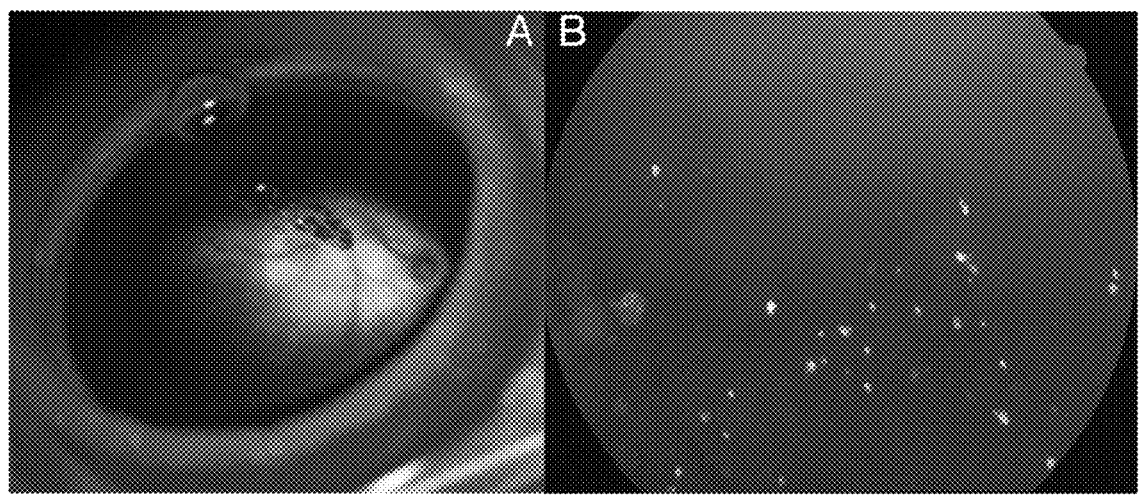
FIG. 8A  FIG. 8B

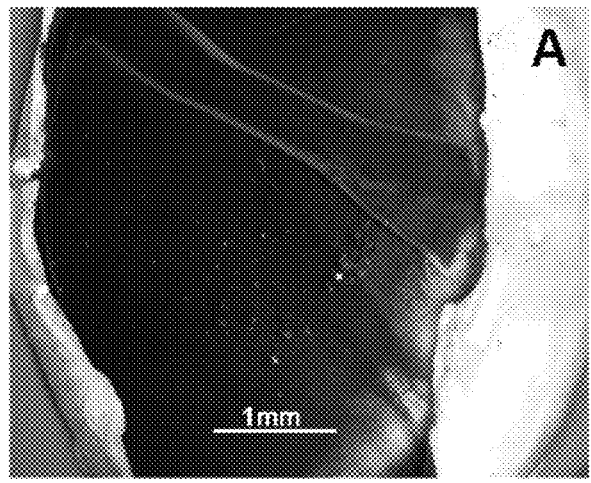
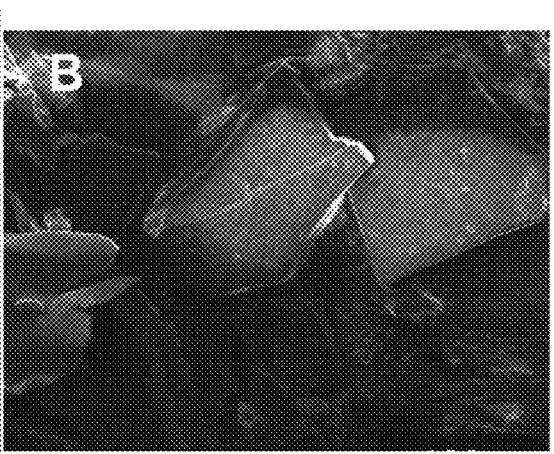
FIG. 9A    FIG. 9B
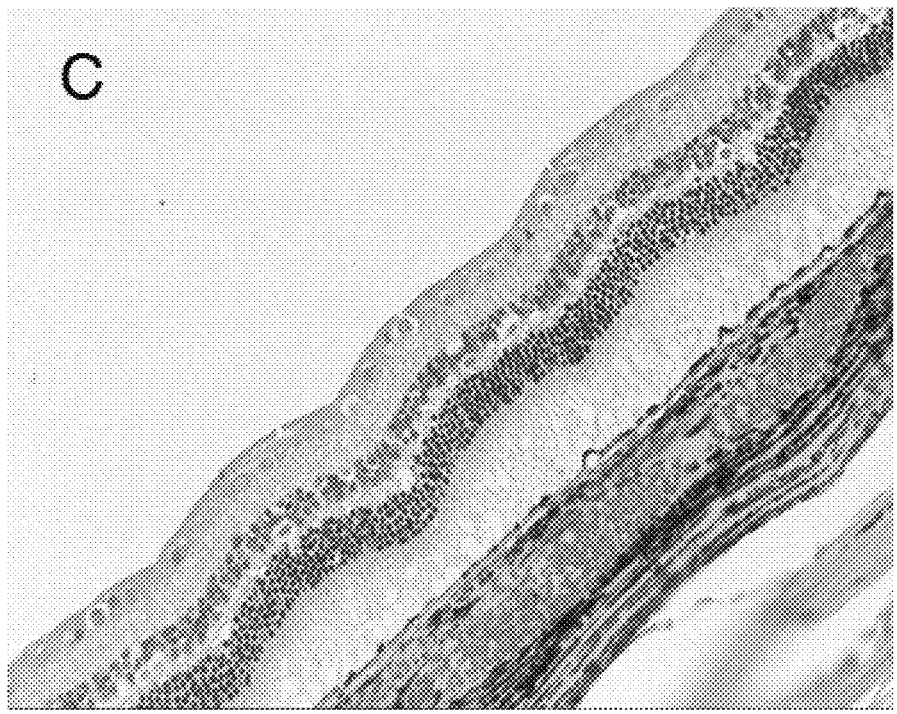
FIG. 9C

- Porous Si microparticles features:
  - Spectral encoding provides self-reporting capability
  - tunable nanostucture for controlling release rate and for accommodating various payloads
  - versatile chemistries for attaching drugs, targeting moieties, and other molecules.

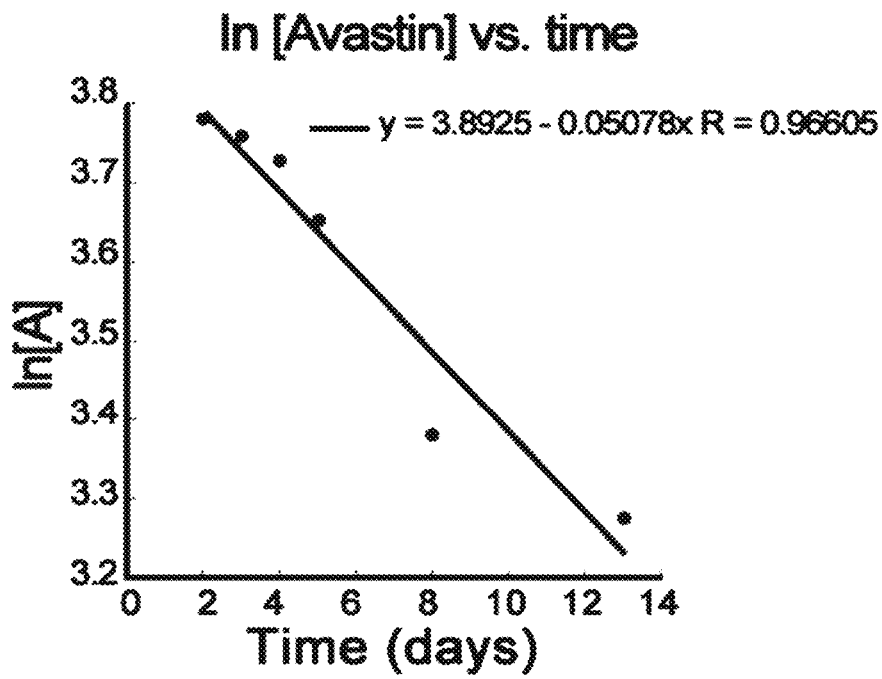

ASSUMPTIONS:
| | |
|---|---|
| Volume of injection (particles + excipient) | 0.1cc |
| Mass of particles injected | 0.0258g |
| Drug half-life in vitreous (AVASTIN) | 5days |
| Drug loading (mg drug/g particle) | 17mg/g |
| Volume of vitreous | 4.5mL |
| Mass of drug injected | 438600nanograms |
| Initial concentration (total drug in particles) | 97466.66667nanograms/mL |

PARTICLE PARAMETERS:
Particles approximated as squares:

| | |
|---|---|
| Thickness | 20microns |
| x-dimension | 20microns |
| Porosity | 50percent |
| Number of particles | 30000particles |
| Density of Si | 2.33g/mL |
| Area per particle | 0.000004cm2 |
| Free volume per particle | 0.000000004cm3 |
| Total free volume | 0.00012cm3 |

RESULTS:
| | |
|---|---|
| Release rate half-life | 13.65 days |
| Theoretical duration of drug release | 303 days |
| Steady-State concentration | 35702.0757nanograms/mL |

*FIG. 13*

MATERIALS AND METHODS FOR DELIVERING COMPOSITIONS TO SELECTED TISSUES

CROSS REFERENCE TO RELATED APPLICATIONS

This application is a continuation of U.S. application Ser. No. 12/668,349, filed Apr. 7, 2010, which is a National Stage Application filed under 35 U.S.C. § 371 and claims priority to International Application No. PCT/US08/69474, filed Jul. 9, 2008, which application claims priority from U.S. Provisional Application Ser. No. 60/948,816, filed Jul. 10, 2008. The application is related to U.S. patent application Ser. No. 11/665,557 filed on Apr. 16, 2007, which is a national stage application of International Patent Application No. PCT/US05/039177, filed Oct. 31, 2005, the contents of which are incorporated herein by reference in their entirety.

STATEMENTS REGARDING FEDERALLY SPONSORED RESEARCH

This invention was made with government support under Grant No. EY007366 and CO037117 awarded by the National Institutes of Health, under F49620-02-1-0288 awarded by the Air Force Office of Scientific Research, and under DMR 0503006 awarded by the National Science Foundation. The government has certain rights in the invention.

TECHNICAL FIELD

The invention relates to delivery systems and, more particularly, to a device that can deliver preprogrammed quantities of a composition over time without the need for external power or electronics.

BACKGROUND

Drug delivery to a location of infection, disease or a disorder to ameliorate symptoms or cure the disease and disorder are important.

SUMMARY

Provided herein are minimally invasive controlled drug delivery systems and methods for use in delivery of a particular drug or drugs to the eye that include porous film or porous film particles having pores configured and dimensioned to at least partially receive at least one drug therein. Embodiments include devices and methods for treating intraocular diseases where porous film particles impregnated with a particular drug are sized and configured to permit intraocular injection of the loaded porous film particles. Other embodiments include devices and methods for treating extraocular diseases, where one of a porous film, biodegradable polymer replica, porous $SiO_2$-polymer composite, or porous Si-polymer composite impregnated with a particular drug is configured to contact a portion of the eye, such as the ocular surface or retrobulbar surface, and controllably release the drug for surface delivery of the drug. Advantageously, release of the drug is also monitorable such that the amount of drug remaining in the porous substrate can be accurately quantified.

The disclosure provides a composition comprising: a silicon material comprising a plurality of pores selectively dimensioned to obtain a desired reflective wavelength and/or rate of drug delivery; and a drug or biologically active material within the pores. In one embodiment, the silicon material comprises a silicon dioxide material. In another embodiment, the material comprises a particulate size of between about 1 µm and 100 µm. The composition can further comprises a polymeric material capping the pores.

The disclosure also provides a multilayer silicon composition comprising a silicon material; a first surface and a second surface on the silicon material; a plurality of pores of a first tunable size on the first surface; a plurality of pores of a second tunable size on the second surface; and a drug or biological agent disposed within the pores on the first and/or second surface. In one embodiment, the silicon composition comprises a particle size between 1 µm and 100 µm. In one embodiment, the silicon material is a silicon dioxide. In yet another embodiment, the composition further comprises a polymer capping the pores on the first side and/or second side.

The disclosure further provides a method of preparing a device for controlled drug delivery to a location of the eye comprising: providing a porous nanostructured silicon-containing template having pores configured to receive a particular drug, said template being sized and configured to be delivered into or upon a surface of the eye; and loading the template with the drug. The method can further comprise providing one of a silicon template, a $SiO_2$ template, and a $SiO_2$/polymer composite template. In yet another embodiment, the method can further comprise disposing one of an organic polymer, an inorganic polymer, and a bio polymer in the template. In yet a further embodiment, the method can comprise removing the silicon-containing template from the polymer by one of chemical corrosion and dissolution. The method can further comprise sizing and configuring the template to be a carrier configured to be included in a contact lens. The method can comprise placing the contact lens in abutment with a front extraocular surface. In one embodiment, the method comprises
sizing and configuring the template to be a scleral plaque for the retrobulbar surface of the eye. The method can comprise suturing the scleral plaque to the retrobulbar surface. The method can comprise injecting the particles intraocularly. The method can comprise configuring the particles to have a monitorable optical response depending on a quantity of drug disposed in the pores. In yet another embodiment, the method can further comprise trapping the drug or drugs in the pores by oxidizing the porous template around the drug or drugs. The oxidizing can be performed at repeated intervals by performing layered oxidation. For example, a biological agent or drug can be trapped in the pores by controlled addition of oxidants. Oxidation of the freshly prepared (hydride-terminated) porous Si material results in an effective shrinking of the pores. This occurs because the silicon oxide formed has a larger volume than the Si starting material. If a drug is also present in the solution that contains the oxidant, the drug becomes trapped in the pores.

The disclosure also provides a minimally invasive controlled drug delivery device for delivering a particular drug or drugs to a particular location of the eye, said device comprising: a porous film template having pores configured and dimensioned to at least partially receive at least one drug therein; and wherein said template is dimensioned to be delivered into or onto the eye.

The disclosure provides a device for the controlled release of an active ingredient comprising: a) a polymer layer comprising a plurality of nano-apertures; b) a base comprising a non-porous substrate layer; and c) at least one reservoir juxtaposed between the polymer layer and the base, wherein the reservoir is in fluid communication with the nano-apertures of the polymer layer and is configured to contain an active ingredient.

The disclosure further provides a method of producing a hydrophilic, porous silicon oxide substrate comprising heating a porous silicon substrate to a temperature above 80° C. in the presence of an agent suitable for oxidizing the silicon substrate thereby producing a hydrophilic, porous silicon oxide substrate.

The disclosure also provides a method of producing a hydrophobic, porous silicon substrate comprising heating a porous silicon substrate to a temperature above 80° C. in the presence of an agent suitable for hydrosilylating the silicon substrate thereby producing a hydrophobic, porous silicon substrate.

The disclosure provides a pulse therapy method for treating a subject, the method comprising: a) identifying a subject having a condition and selecting one or more active ingredients suitable for treating the condition; b) correlating the quantity and type of active ingredients with a pulse therapy dosing profile suitable for treating the condition; c) configuring a device of the disclosure to obtain a device suitable for delivering the dosing profile of b) to the subject; and e) implanting or explanting the device in or on a target tissue associated with the subject.

BRIEF DESCRIPTION OF DRAWINGS

FIG. 7A-D depicts intravitreal injections of porous Si particles. (A) is a photograph taken under a surgical microscope immediately after intravitreal injection of fresh porous Si particles. Particles can be observed suspended in the center of the vitreous. A few small air bubbles mixed with the porous Si particles are present at the top of the vitreous cavity. (B) is a fundus photograph taken one week after the injection, showing porous Si particles dispersed in the vitreous. (C) is a fundus photograph taken 2 weeks after injection, indicating that most of the particles have disappeared and those remaining were barely observable. (D) depicts a light microscopic graph showed normal retina detached from the retinal pigment epithelium during the histology processing. (25×, H&E staining).

FIG. 8A-B provides images of intravitreal hydrosilylated Si particles. (A) is a photograph taken under a surgical microscope immediately after intravitreal injection of hydrosilylated porous Si particles. Particles can be observed suspended in the center of the vitreous. (B) is a fundus photograph obtained 3 months after injection. The particles are dispersed in the vitreous and many demonstrated a distinctive blue color indicative of partial degradation and dissolution.

FIG. 9A-C provides images of ocular tissue following Si particle injection. (A) shows a surgical microscope image of a dissected rabbit eye cup, with hydrosilylated porous Si particles distributed on a normal looking retina. Photograph was obtained 4 months after injection. Two retina folds are present, caused during dissection. (B) shows a scanning electron microscope image of the hydrosilylated porous Si particles sampled from a rabbit eye 4 months after intravitreal injection. The sharp edges and pitted surface of the particles indicate a very slow erosion process. (C) shows a light microscopic photograph of the retina and choroid from a rabbit eye harvested 9 months after intravitreal injection of hydrosilylated porous Si particles. Normal chorioretinal morphology and structures are observed. (62.5×, H&E staining).

FIG. 13 provides data for the release profile of Avastin from a Si microparticle provided herein.

DETAILED DESCRIPTION

Figure 1A:
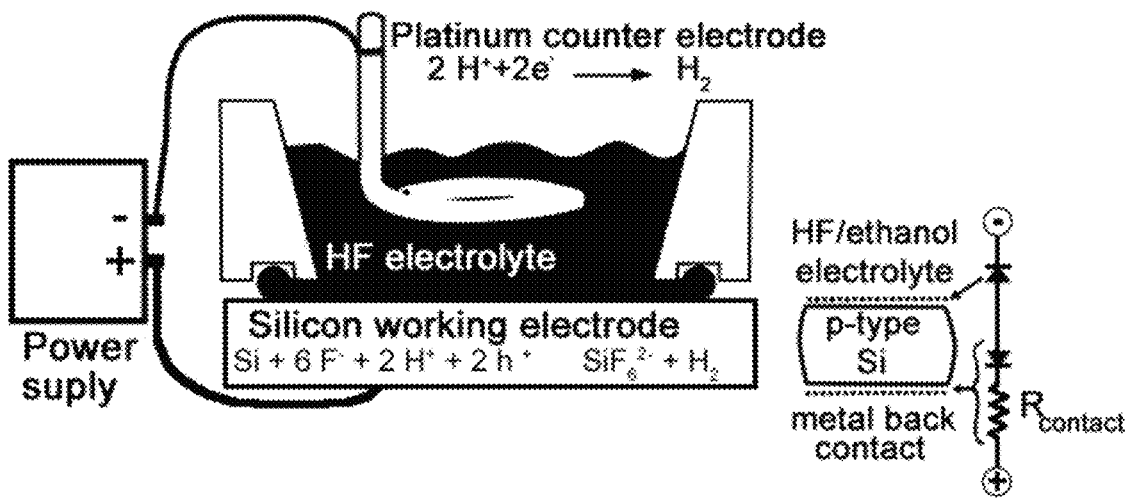
FIG. 1A-B show methods and reactions for generating porous Si. (A) Shows a schematic of the etch cell used to prepare porous Si. The electrochemical half reactions are shown, and the equivalent circuit for etching of a p-type Si wafer is shown at right. (B) represents a chemical reaction for the oxidation of the porous Si around a candidate molecule according to one embodiment of the disclosure.

As used herein and in the appended claims, the singular forms "a," "and," and "the" include plural referents unless the context clearly dictates otherwise. Thus, for example, reference to "a pore" includes a plurality of such pores and reference to "the drug" includes reference to one or more drugs known to those skilled in the art, and so forth.

Also, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions, the exemplary methods, devices and materials are described herein.

The publications discussed above and throughout the text are provided solely for their disclosure prior to the filing date of the present application. Nothing herein is to be construed as an admission that the inventors are not entitled to antedate such disclosure by virtue of prior disclosure.

The ability to deliver drugs locally to the site of need and over a prolonged period of time is important as a therapeutic method for many ailments and diseases. Many drugs are more effective if delivered at a specific site since they can be delivered in concentrated dosages at the point of interest, while maintaining an overall low dosage within the total body. Additionally, many drugs cannot be delivered by oral means because the molecules are too fragile to survive the digestive process, or because the molecules do not pass efficiently through the walls of the digestive organs. Some drug therapies require long term dosing over the course of many months or years requiring frequent visits to a clinician for treatment. Furthermore, some drugs require delivery in places that are inconvenient for injection, such as in the eye or in internal organs. In all these cases, sustained drug delivery through an implant or attached device would be of great benefit to patients undergoing treatment.

An important application of drug delivery implant is age related macular degeneration (AMD). Age related macular degeneration is the leading cause of blindness in people over age 65. The National Eye Institute estimates that there are 1.6 million individuals with AMD in the United States alone. Macular degeneration is the physical disturbance of the center of the retina called the macula, the part of the retina which is capable of the most acute and detailed vision. Currently, there is no known cure for AMD. However, new therapies are being developed which show promise in controlling the progression of the disease. Some of these treatments include frequent administration of protein-based drug formulations such as Lucentis (ranibizumab) and Avastin (bevacizumab) directly into the eye. Since these drugs consist of large protein molecules which cannot be administered through oral formulations, patients suffering from AMD have to receive injections directly into their eyes once every month. The highly invasive nature of the treatment and limitations in controlling an effective drug concentration in the eye over a prolonged period of time still leave these delivery methods far from ideal.

In addition to AMD, diabetic retinopathy, retinovasclar disease, and other types of retinal degenerations are amenable to treatment by drug delivery implant. This is because many of those diseases also need local therapy with the same types of compounds that are used for AMD. Treating diseases associated with intraocular scarring such as retinal detachment (PVR) and glaucoma can also be accomplished through sustained release of drug within the eye to prevent unwanted proliferation.

Delivery of drugs into vitreous via liposomes or slow release crystalline lipid prodrugs extend the drug vitreous half-life, but traditional liposomes or self-assembling liposomes often decrease vitreous clarity when used, cannot be easily customized to release drugs with different physicochemical properties, and do not "report" drug release information. Accordingly, the current state of art does not provide a satisfactory way to construct a small device and implement methods for the delivery of a drug in a predetermined time dependent manner.

Each of the features and teachings disclosed below can be utilized separately or in conjunction with other features and teachings to provide a drug delivery device for delivering time dependent dosing. Representative examples of the disclosure, which examples utilize many of these additional features and teachings both separately and in combination, will now be described in further detail with reference to the attached drawings. This detailed description is merely intended to teach a person of skill in the art further details for practicing aspects of the present teachings and is not intended to limit the scope of the invention. Therefore, combinations of features and steps disclosed in the following detail description may not be necessary to practice the invention in the broadest sense, and are instead taught merely to particularly describe representative examples of the present teachings.

Moreover, the various features of the representative examples and the dependent claims may be combined in ways that are not specifically and explicitly enumerated in order to provide additional useful embodiments of the present teachings. In addition, it is expressly noted that all features disclosed in the description and/or the claims are intended to be disclosed separately and independently from each other for the purpose of original disclosure, as well as for the purpose of restricting the claimed subject matter independent of the compositions of the features in the embodiments and/or the claims. It is also expressly noted that all value ranges or indications of groups of entities disclose every possible intermediate value or intermediate entity for the purpose of original disclosure, as well as for the purpose of restricting the claimed subject matter.

As an initial starting point it is important to understand the difference between silicon, silicon oxide and silica (i.e., silicon dioxide). This is mentioned because there is a fundamental difference in the compositions, uses and biological activity of these materials.

Silicon is the chemical element that has the symbol Si and atomic number 14. Silicon occasionally occurs as the pure free element in nature, but is more widely distributed as various forms of silicon dioxide (silica) or silicates. Silicon is used in the electronics industry where substantially pure and highly pure silicon are used for the formation of wafers. Pure silicon is used to produce ultra-pure silicon wafers used in the semiconductor industry, in electronics and in photovoltaic applications. Ultra-pure silicon can be doped with other elements to adjust its electrical response by controlling the number and charge (positive or negative) of current carriers. Such control is desirable for transistors, solar cells, integrated circuits, microprocessors, semiconductor detectors and other semiconductor devices which are used in electronics and other high-tech applications. In photonics, silicon can be used as a continuous wave Raman laser medium to produce coherent light. Hydrogenated amorphous silicon is used in the production of low-cost, large-area electronics in applications such as LCDs, and of large-area, low-cost thin-film solar cells. Accordingly, most commonly purchased silicon is in the form of silicon wafers. Silicon when metabolized by the body is converted to silane, a compound that when accumulated has toxic effects.

Silicon oxide typically refers to a silicon element linked to a single reactive oxygen species (e.g., a radical). Such silicon oxide compounds are useful for the additional of carbon or other desirable elements wherein a bond is formed between the reactive oxygen and the desired element or chemical side chain. Silicon oxides are useful for the formation of hydrogenated silicon oxycarbide (H:SiOC) films having low dielectric constant and a light transmittance. Such Si—O—X (wherein X is any suitable element other than oxygen) compounds are formed using complex reactions including reacting a methyl-containing silane in a controlled oxygen environment using plasma enhanced or ozone assisted chemical vapor deposition to produce the films. In contrast, a dioxide (further described below) comprises two (2) oxygens linked to a silicon atom.

Silicon dioxide refers to the compound $SiO_2$ (sometime referred to as silica). Silicon dioxide is formed when silicon is exposed to oxygen (or air). A thin layer (approximately 1 nm or 10 Å) of so-called 'native oxide' is formed on the surface when silicon is exposed to air under ambient conditions. Higher temperatures and alternate environments are used to grow layers of silicon dioxide on silicon. Silicon dioxide is inert and harmless. When silica is ingested orally, it passes unchanged through the gastrointestinal tract, exiting in the feces, leaving no trace behind. Small pieces of silicon dioxide are equally harmless, so long as they are not large enough to mechanically obstruct the GI tract or fluid flow, or jagged enough to lacerate the GI lining, vessel or other tissue. Silicon dioxide produces no fumes and is insoluble in vivo. It is indigestible, with zero nutritional value and zero toxicity. Silicon dioxide has covalent bonding and forms a network structure. Hydrofluoric acid (HF) is used to remove or pattern silicon dioxide in the semiconductor industry.

Silicon is an essential trace element that is linked to the health of bone and connective tissues. The chemical species of relevance to the toxicity of porous Si are silane ($SiH_4$) and dissolved oxides of silicon; three important chemical reactions of these species are given in Eq. (1)-(3). The surface of porous Si contains Si—H, $SiH_2$, and $SiH_3$ species that can readily convert to silane. Silane is chemically reactive (Eq. (1)) and toxic, especially upon inhalation. Like silane, the native $SiH_x$ species on the porous Si surface readily oxidize in aqueous media. Silicon itself is thermodynamically unstable towards oxidation, and even water has sufficient oxidizing potential to make this reaction spontaneous Eq. (2). The passivating action of $SiO_2$ and Si—H (for samples immersed in HF solutions) make the spontaneous aqueous dissolution of Si kinetically slow. Because of its highly porous nanostructure, oxidized porous Si can release relatively large amounts of silicon-containing species into solution in a short time. The soluble forms of $SiO_2$ exist as various silicic acid compounds with the orthosilicate ($SiO_4^{4-}$) ion as the basic building block (Eq. (3)), and these oxides can be toxic in high doses. Because the body can handle and eliminate silicic acid, the important issue with porous Si-based drug delivery systems is the rate at which they degrade and resorb.

$$SiH_4 + 2H_2O \rightarrow SiO_2 + 4H_2 \quad (1)$$

$$Si + O_2 \rightarrow SiO_2 \quad (2)$$

$$SiO_2 + 2H_2O \rightarrow Si(OH)_4 \quad (3)$$

Surface chemistry plays a large role in controlling the degradation properties of porous Si in vivo. After Si is electrochemically etched, the surface is covered with reactive hydride species. These chemical functionalities provide a versatile starting point for various reactions that determine the dissolution rates in aqueous media, allow the attachment of homing species, and control the release rates of drugs. The two most important modification reactions are chemical oxidation (Eq. (2)) and grafting of Si—C species.

The various embodiments provided herein are generally directed to systems and methods for producing a drug delivery device that can deliver time dependent dosing without the need for electronics or power. Accordingly, the disclosure recognizes and addresses an important and unmet medical need for a minimally invasive, controllable and monitorable drug delivery system and methods of using the system that would enable long acting local treatment of both extraocular and intraocular diseases.

Traditional methods of intraocular drug delivery include the use of liposomes or self-assembling liposomes, which often decrease vitreous clarity when used, cannot be easily customized to release drugs with different physicochemical properties, and do not "report" drug release information.

Advantageously, the disclosure provides devices and methods for treating both intraocular and extraocular diseases that promote sustained release of a pharmacological candidate, or drug, that is impregnated on nanostructured silicon, such as Si, $SiO_2$, polymer-templated, Si/polymer, or $SiO_2$/polymer composites.

In one aspect, the devices and methods are also self-reporting such that drug release and quantity remaining can be monitored. Embodiments include minimally invasive, self-reporting, controlled delivery systems for delivering a drug or drugs to surfaces of the eyes, both the ocular surface (cornea and conjunctiva) and the scleral surface, as well as intraocular portions of the eye, including the retina, choroids, lens, ciliary body, anterior chamber, and vitreous. Such devices include not only Si photonic crystals that include an active ingredient, but also biodegradable polymer imprints made from porous silicon templates.

For intraocular diseases, such as glaucoma, age-related macular degeneration (ARMD), choroidal neovascularization (CNV), uveitis, diabetic retinopathy, retinovasclar disease, and other types of retinal degenerations, drug delivery to the vitreous, retina, and choroid is a challenging task due to the formidable obstacles posed by the blood-retinal barrier and the tight junctions of the retinal pigment epithelium. Only small fractions of drug administered systemically reach the target, requiring large and potentially toxic doses when delivered systemically. Another challenge to retinal drug delivery is the fact that drug levels should be sustained for prolonged periods at the target site. This is difficult using intravitreal injections because the short half-life of most intravitreal injectable drugs. Intraocular implants have provided sustained vitreoretinal drug levels for treating certain retinal diseases. However, this route demands intraocular surgery that is known to cause intraocular complications when placing and replacing the implant.

For ocular surface diseases, such as viral keratitis, chronic allergic conjunctivitis, glaucoma, and scleritis, some of the same problems persist. Systemic administration of drug requires potentially toxic doses, and topical treatments have a short half-life, requiring numerous and frequent doses. For treating ocular surface diseases biodegradable polymer imprints may be made from porous silicon templates. The silicon-free polymer may be used in drug delivery contact lenses or implants at an appropriate location on or associated with the eye, including the ocular surface and retrobulbar surface.

Photonic crystals have widespread application in optoelectronics, chemical and biological sensors, high-throughput screening, and drug delivery applications. These photonic crystals are especially advantageous because of the relative ease with which the optical properties, pore size, and surface chemistry can be manipulated. Moreover, position, width, and intensity of spectral reflectivity peaks may be controlled by the current density waveform and solution composition used in the electrochemical etch, thus rendering possible the preparation of films of porous Si photonic crystals that display any color within the visible light band with high color saturation, which is a desirable feature for information displays.

The term photonic crystal refers to a material in which a spatially repeating pattern produces a distinctive spectral pattern. A photonic crystal comprises small porous silicon particles that have been machined and sized to small crystals for intraocular injection.

The disclosure provides compositions and methods for injection of porous microscopic nanostructured silicon particles impregnated with a particular drug or drugs. While the disclosure contemplates use of numerous porous microscopic particles, typical particles include porous silicon or silicon dioxide particles (referred to as “smart dust”), which are nanostructure that allows maintenance of sustained intraocular therapeutic drug levels with minimal invasiveness and elimination of systemic side effects. In addition to configuring the nanostructure to suit individual applications, the disclosure also contemplates chemically modifying the particles and the particular drug or drugs to tune and control release profiles of the particles. Intraocular injection allows monitoring of drug levels non-invasively.

Porous silicon is advantageous in that porous silicon films have a large free volume (typically 50-80%). Thus having a high capacity for a drug can be custom designed at the nanoscale to deliver one or more drugs at a variety of customizable release rates and the photonic properties of a nanostructured material as a means to non-invasively determine the rate and amount of drug delivered. The porous silicon photonic crystal particles of the disclosure can be impregnated with a drug or plurality of drugs, and subsequently introduced into the retina, choroids, lens ciliary body, anterior chamber, and vitreous of the eye via injection. For details of coded photonic particles and methods of preparing the same, see published U.S. application serial numbers: 20050042764 entitled, “Optically encoded particles,” 20050009374 entitled, “Direct patterning of silicon by photoelectrochemical etching,” 20070148695 entitled “Optically encoded particles, system and high-throughput screening,” and 20070051815 entitled “Optically encoded particles with grey scale spectra,” which are incorporated herein by reference.

The “smart dust” photonic crystal particles can be optimized for intravitreal delivery of one or more of a vast array of drugs including anti-cancer drugs and other small molecule drugs, inhibitory nucleic acids, peptides and polypeptides. For example, the disclosure demonstrates pigment epithelium derived factor (PEDF), an 8-mer peptide fragment of urokinase (uPA), dexamethasone, and a host of other drugs, small molecules, proteins (e.g., antibodies such as bevacizumab and Fab fragments of antibodies such as ranibizumab), peptides, and nucleic acids can be used. These smart dust photonic crystals may be impregnated with drugs by either trapping one or more of the drugs in porous Si smart dust, or the pores themselves may be chemically modified to bind the candidate drug.

Photonic crystals are produced from porous silicon and porous silicon/polymer composites, or porous Si film or polymer replica or Si-polymer composite may be generated as a sheet for an exoplant. Pulsed electrochemical etching of a silicon chip produces a multilayered porous nanostructure. A convenient feature of porous Si is that the average pore size can be controlled over a wide range by appropriate choice of current, HF concentration, wafer resistivity, and electrode configuration used in the electrochemical etch. This tunability of the pore dimensions, porosity, and surface area is especially advantageous.

The thickness, pore size, and porosity of a given film is controlled by the current density, duration of the etch cycle, and etchant solution composition. In addition, a porous silicon film can be used as a template to generate an imprint of biologically compatible or bioresorbable materials. The porous silicon film or its imprint possess a sinusoidally varying porosity gradient, providing sharp features in the optical reflectivity spectrum that can be used to monitor the presence or absence of chemicals trapped in the pores. It has been shown that the particles (smart dust) made from the porous silicon films by mechanical grinding or by ultrasonic fracture still carry the optical reflectivity spectrum.

Porous Si is a product of an electrochemical anodization of single crystalline Si wafers in a hydrofluoric acid electrolyte solution. Pore morphology and pore size can be varied by controlling the current density, the type and concentration of dopant, the crystalline orientation of the wafer, and the electrolyte concentration in order to form macro-, meso-, and micropores. Pore sizes ranging from 1 nm to a few microns can be prepared. The type of dopant in the original silicon wafer is important because it determines the availability of valence band holes that are the key oxidizing equivalents in the reaction shown in FIG. 1. In general the relationships of dopant to morphology can be segregated into four groups based on the type and concentration of the dopant: n-type, p-type, highly doped n-type, and highly doped p-type. By “highly doped,” is meant dopant levels at which the conductivity behavior of the material is more metallic than semiconducting. For n-type silicon wafers with a relatively moderate doping level, exclusion of valence band holes from the space charge region determines the pore diameter. Quantum confinement effects are thought to limit pore size in moderately p-doped material. For both dopant types the reaction is crystal face selective, with the pores propagating primarily in the <100> direction of the single crystal. For example, electrochemically driven reactions use an electrolyte containing hydrofluoric acid. Application of anodic current oxidizes a surface silicon atom, which is then attacked by fluoride. The net process is a 4 electron oxidation, but only two equivalents are supplied by the current source. The other two equivalents come from reduction of protons in the solution by surface $SiF_2$ species. Pore formation occurs as Si atoms are removed in the form of $SiF_4$, which reacts with two equivalents of F— in solution to form $SiF_6^{2-}$.

The porosity of a growing porous Si layer is proportional to the current density being applied, and it typically ranges between 40 and 80%. Pores form at the Si/porous Si interface, and once formed, the morphology of the pores does not change significantly for the remainder of the etching process. However, the porosity of a growing layer can be altered by changing the applied current. The film will continue to grow with this new porosity until the current changes.

This feature allows the construction of layered nanostructures simply by modulating the applied current during an etch. For example, one dimensional photonic crystals consisting of a stack of layers with alternating refractive index can be prepared by periodically modulating the current during an etch.

Stain etching is an alternative to the electrochemical method for fabrication of porous Si powders. The term stain etching refers to the brownish or reddish color of the film of porous Si that is generated on a crystalline silicon material subjected to the process. In the stain etching procedure, a chemical oxidant (typically nitric acid) replaces the power supply used in the electrochemically driven reaction. HF is typically used as an ingredient, and various other additives are used to control the reaction. Stain etching generally is less reproducible than the electrochemical process, although recent advances have improved the reliability of the process substantially. Porous Si powders prepared by stain etch are commercially available (http:~vestaceramics.net).

For in vivo applications, it is often desirable to prepare porous Si in the form of particles. The porous layer can be removed from the Si substrate with a procedure commonly referred to as "electropolishing" or "lift-off." The etching electrolyte is replaced with one containing a lower concentration of HF and a current pulse is applied for several seconds. The lower concentration of HF results in a diffusion limited situation that removes silicon from the crystalline Si/porous Si interface faster than pores can propagate. The result is an undercutting of the porous layer, releasing it from the Si substrate. The freestanding porous Si film can then be removed with tweezers or a vigorous rinse. The film can then be converted into microparticles by ultrasonic fracture. Conventional lithography or microdroplet patterning methods can also be used if particles with more uniform shapes are desired.

The ability to easily tune the pore sizes and volumes during the electrochemical etch is a unique property of porous Si that is very useful for drug delivery applications. Other porous materials generally require a more complicated design protocol to control pore size, and even then, the available pore sizes tend to span a limited range. With electrochemically prepared porous Si, control over porosity and pore size is obtained by adjusting the current settings during the etch. Typically, larger current density produces larger pores. Large pores are desirable when incorporating sizable molecules or drugs within the pores. Pore size and porosity is important not only for drug loading; it also determines degradation rates of the porous Si host matrix.

Smaller pores provide more surface area and expose more sites for attack of aqueous media. The smaller porous filaments within the film yield greater dissolution rates, providing a convenient means to control degradation rates of the porous Si host.

Surface chemistry plays a large role in controlling the degradation properties of porous Si in vivo. Immediately after Si is electrochemically etched, the surface is covered with reactive hydride species. These chemical functionalities provide a versatile starting point for various reactions that determine the dissolution rates in aqueous media, allow the attachment of homing species, and control the release rates of drugs. The two most important modification reactions are chemical oxidation (Eq. (2)) and grafting of Si—C species.

With its high surface area, porous Si is particularly susceptible to air or water oxidation. Once oxidized, nanophase $SiO_2$ readily dissolves in aqueous media, and surfactants or nucleophiles accelerate the process. Si—O bonds are easy to prepare on porous Si by oxidation, and a variety of chemical or electrochemical oxidants can be used. Thermal oxidation in air tends to produce a relatively stable oxide, in particular if the reaction is performed at >600° C. Ozone oxidation, usually performed at room temperature, forms a more hydrated oxide that dissolves quickly in aqueous media.

Milder chemical oxidants, such as dimethyl sulfoxide (DMSO, Eq. (4)), benzoquenone, or pyridine, can also be used for this reaction. Mild oxidants are sometimes preferred because they can improve the mechanical stability of highly porous Si films, which are typically quite fragile.

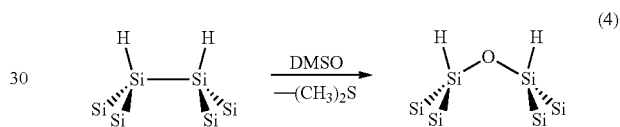

(4)

The mechanical instability of porous Si is directly related to the strain that is induced in the film as it is produced in the electrochemical etching process, and the volume expansion that accompanies thermal oxidation can also introduce strain. Mild chemical oxidants presumably attack porous Si preferentially at Si—Si bonds that are the most strained, and hence most reactive. As an alternative, nitrate is a stronger oxidant, and nitric acid solutions are used extensively in the preparation of porous Si particles from silicon powders by chemical stain etching.

Slow oxidation of the porous Si surface by dimethyl sulfoxide (DMSO), when coupled with dissolution of the newly formed oxide by HF, is a mild means to enlarge the pores in porous Si films. Aqueous solutions of bases such as KOH can also be used to enlarge the pores after etching. Electrochemical oxidation, in which a porous Si sample is anodized in the presence of a mineral acid such as $H_2SO_4$, yields a fairly stable oxide. Oxidation imparts hydrophilicity to the porous structure, enabling the incorporation and adsorption of hydrophilic drugs or biomolecules within the pores. Aqueous oxidation in the presence of various ions including $Ca^{2+}$ generates a calcified form of porous Si that has been shown to be bioactive and is of particular interest for in vivo applications. Calcification can be enhanced by application of a DC electric current.

The porous smart silicon dust can be oxidized to increase stability and injected into animal eyes. The smart silicon dust can be variously modified to be a long-lasting intraocular drug delivery vehicle to carry various therapeutic compounds. In addition, biodegradable porous polymer imprints made from porous silicon templates can be used as a drug delivery implant to be placed at an appropriate location in the eye. The drug can be added into the imprint solution before casting or engineered into the pores after casting.

Carbon grafting stabilizes porous Si against dissolution in aqueous media, but the surface must still avoid the non-specific binding of proteins and other species that can lead to opsonization or encapsulation. Reactions that place a polyethylene glycol (PEG) linker on a porous Si surface have been employed to this end. A short-chain PEG linker yields a hydrophilic surface that is capable of passing biomolecules into or out of the pores without binding them strongly. The distal end of the PEG linker can be modified to allow coupling of other species, such as drugs, cleavable linkers, or targeting moieties, to the material.

The oxides of porous Si are easy to functionalize using conventional silanol chemistries. When small pores are present (as with p-type samples), monoalkoxydimethylsilanes (RO—Si(Me)$_2$-R') can be more effective than trialkoxysilanes ((RO)$_3$Si—R') as surface linkers. This is because trialkoxysilanes oligomerize and clog smaller pore openings, especially when the reagent is used at higher concentrations.

Whereas Si—C chemistries are robust and versatile, chemistries involving Si—O bonds represent an attractive alternative two reasons. First, the timescale in which highly porous SiO$_2$ is stable in aqueous media is consistent with many short-term drug delivery applications-typically 20 min to a few hours. Second, a porous SiO$_2$ sample that contains no additional stabilizing chemistries is less likely to produce toxic or antigenic side effects. If it is desired that the porous Si material be stable in vivo for long periods (for example, an extended release formulation or an in vivo biosensor), Si—C chemistries such as hydrosilylation with endcapping or thermal carbonization with acetylene is useful. If a longer-lived oxide matrix is desired, silicon oxides formed at higher temperatures (>700° C.) are significantly more stable in aqueous media than those formed at lower temperatures or by ozone oxidation.

Either silicon smart dust or the episcleral one-way releasing plaque of biodegradable polymer imprint of silicon smart dust provide a device and method for intravitreal drug delivery that promotes sustained intraocular therapeutic drug levels with minimal invasiveness and elimination of systemic side effects. Impregnation of the porous material may proceed in several ways.

The candidate drug may be "physically" trapped within the pores, or, the pores themselves may be chemically modified to bind the candidate drug.

Figure 1B:
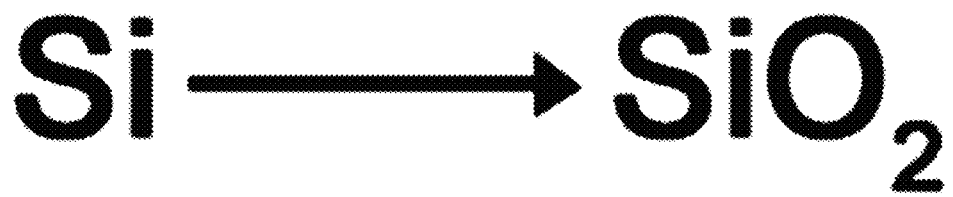

More specifically, "physical trapping" is similar to building a ship in a bottle, where the "ship" is the candidate drug and the "bottle" is the nanometer-scale pores in the porous Si matrix. Small molecules can be trapped in the porous matrix by oxidizing the porous Si around the molecule. The relevant reaction is illustrated in FIG. 1, where "O" in the equation is a molecular oxidant such as O2, dimethyl sulfoxide, hydrogen peroxide, or water. Since oxidation of silicon adds two atoms of oxygen per atom of Si to the material, there is a significant increase in volume of the matrix upon oxidation. This has the effect of swelling the pore walls and shrinking the free volume inside the pores, and under the appropriate conditions, molecules present in the pores during oxidation become trapped in the oxide matrix. One aspect of the trapping process is the increased concentration of the active ingredient which occurs during the trapping process. The crystals may present a negatively charged environment and an active ingredient, such as proteins and other drugs, may be concentrated in the crystals to levels much higher than the free concentration of the active ingredient in solution. This can result in 10 to 100 fold or more increase in active ingredient concentration when associated with a crystal. For example, Avastin which has a commercial concentration of 2.5 mg per 0.1 cc can be concentrated by association with the crystal structures described herein. The oxidizing can be performed at repeated intervals by performing layered oxidation. For example, a biological agent or drug can be trapped in the pores by controlled addition of oxidants. Oxidation of the freshly prepared (hydride-terminated) porous Si material results in an effective shrinking of the pores. This occurs because the silicon oxide formed has a larger volume than the Si starting material. If a drug is also present in the solution that contains the oxidant, the drug becomes trapped in the pores.

Furthermore the porous silicon oxide can comprise a higher concentration of a biological agent or drug (e.g., Avastin) than a non-oxidized Si hydride material. For example, the oxide treatment causes the oxidized porous Si material to absorb larger quantities of the drug Avastin than are absorbed by the freshly prepared (hydride-terminated) porous Si material.

The free volume in a porous Si film is typically between 50 and 80%. Oxidation should reduce this value somewhat, but the free volume is expected to remain quite high. Most of the current drug delivery materials are dense solids and can deliver a small percentage of drug by weight. The amount of drug that can be loaded into the porous Si material is expected to be much larger than, for example, surface-modified nanoparticles or polylactide (PLA) polymers. Experiments can quantify the amount of each of the drugs that can be loaded into the smart dust delivery vehicle.

Figure 2:
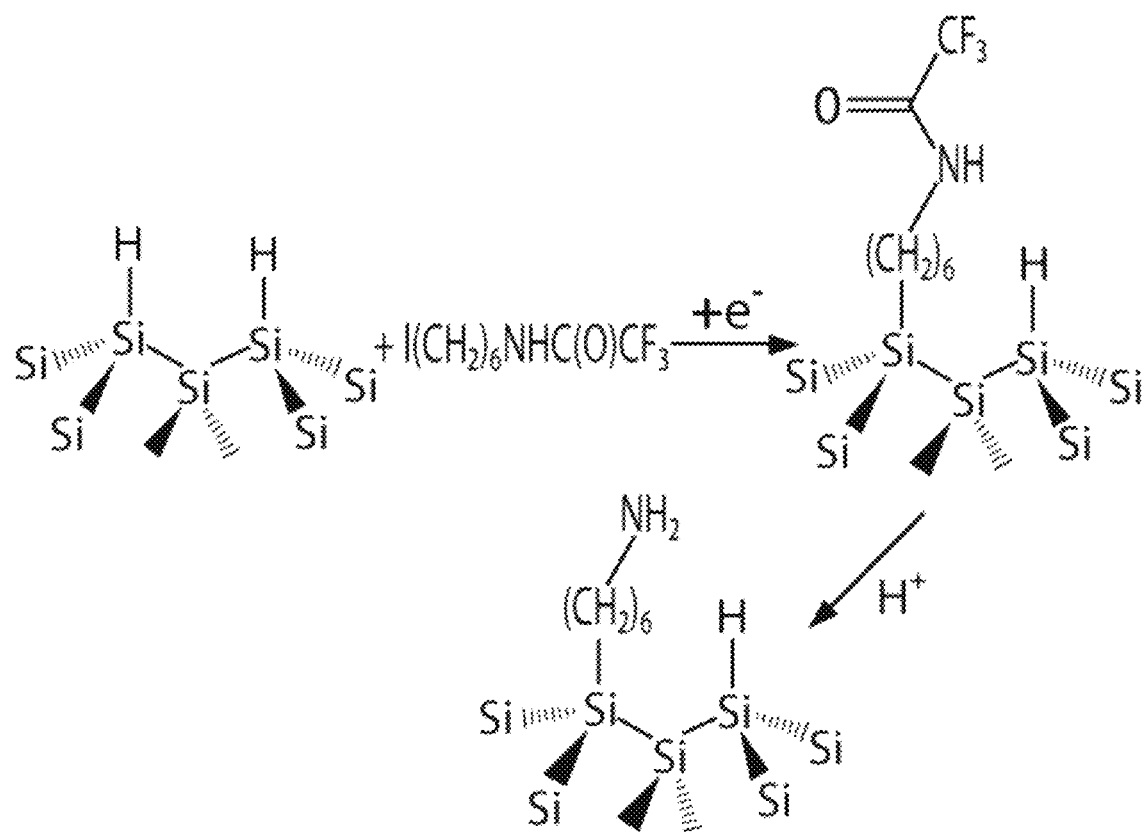
FIG. 2 illustrates a chemical modification reaction whereby a candidate molecule is attached to an inner pole wall according to another embodiment of the invention

During chemical modification, a molecule is attached to the inner pore walls via covalent bonds. In the porous Si system, proteins, DNA, and various small molecules can be attached following several different procedures. One embodiment uses electrochemical modification. For example, reduction of 1-iodo-6-(trifluoroacetylamino) hexane at a p-type porous silicon cathode leads to attachment of the trifluoroacetamidohexyl group. Subsequent acid-catalyzed hydrolysis should lead directly to the surface-bound amine species. The reactions are represented by the equation illustrated in FIG. 2.

The surface amine can then be functionalized with a drug, polypeptide or peptide. As demonstrated in the specific non-limiting examples, below, the surface amine is functionalized with an 8-mer peptide fragment of uPA using standard peptide coupling methods.

Various approaches to load a molecular payload into a porous Si host have been explored, and they can be grouped into the following general categories: covalent attachment, physical trapping, and adsorption.

Covalent attachment provides a convenient means to link a biomolecular capture probe to the inner pore walls of porous Si for biosensor applications, and this approach can also be used to attach drug molecules. As described elsewhere herein, linking a biomolecule via Si—C bonds tends to be a more stable route than using Si—O bonds due to the susceptibility of the Si—O species to nucleophilic attack.

The versatility of the hydrosilylation reaction for preparing functional porous Si surfaces was recognized early in the history of porous Si surface chemistry. One of the more common approaches is to graft an organic molecule that contains a carboxyl species on the distal end of a terminal alkene. The alkene end participates in the hydrosilylation reaction, bonding to the Si surface and leaving the carboxy-terminus free for further chemical modification. A favorite linker molecule is undecylenic acid, which provides a hydrophobic 10 carbon aliphatic chain to insulate the linker from the porous Si surface. The drug payload can be attached directly to the carboxy group of the alkene, or it can be further separated from the surface with a PEG linker. Due to the stability of the Si—C bond, hydrosilylation is good way of attaching a payload to porous Si. The payload is only released when the covalent bonds are broken or the supporting porous Si matrix is degraded. For drug delivery this introduces a complication in that the drug may not release from the linker, resulting in a modified version of the drug being introduced into the body. In addition, a drug may be susceptible to attack by silane generated during the degradation of the porous Si scaffolding or by residual reactive species on the porous Si material itself.

If the drug to be trapped is relatively robust, it can be locked into place by oxidation of the porous Si host matrix. The locking procedure takes advantage of the fact that when porous Si is oxidized to $SiO_2$ there is a volume expansion to accommodate the extra oxygen atoms. This volume expansion serves to shrink the pores, trapping anything that happens to be in them at the time. High pH and nucleophilic nature of ammonia enhance oxidation of freshly etched porous Si in aqueous solutions. Similar oxidation can be induced by vapor phase pyridine. Nucleophilic groups present on drug payloads may also participate in this reaction, as can oxidizing species such as quinones. The silicic acid generated during dissolution Eq. (3) can participate in sol-gel type reactions—essentially reprecipitation of the silicic acid, but in the form of various inorganic silicates. Common ions such as $Ca^{2+}$ and $Mg^{2+}$ in solution can participate in silicate precipitation reactions Eq. (5), and these types of precipitates are known to be bioactive.

$$Si(OH)_4 + 2Ca^{2+} \rightarrow Ca_2SiO_4 + 4H^+ \qquad (5)$$

Once formed, mild thermal treatments can be used to dehydrate the oxide or silicate matrix. Heating tends to densify and rigidify the structure by forming strong Si—O—Si linkages (Eq. (6)).

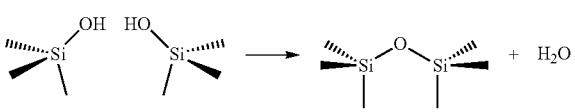

(6)

As-formed porous Si has a hydride-terminated surface that is very hydrophobic. Oxidized porous Si is hydrophilic, and chemically modified porous Si surfaces can be hydrophobic, hydrophilic, or both (amphiphilic), depending on the specific functional group(s) attached. The nature of the surface plays a critical role in determining the amount of drug that can be loaded and the rate at which it is released. Silicon oxide surfaces tend to present a negative surface charge to an aqueous solution due to the low pKa of $SiO_2$. Often referred to as "electrostatic adsorption," attractive coulombic forces from this negative surface provide a means to extract positively charged ions from solution and concentrate them at the interface.

Whereas covalent attachment and oxidative trapping approaches described above tend to trap their payloads fairly irreversibly, electrostatic adsorption represents essentially an ion exchange mechanism that holds molecules more weakly. Electrostatics is a useful means to affect more rapid drug delivery, as opposed to covalent or physical trapping approaches that release drug over a period of days, weeks, or months.

The affinity of a porous Si particle for a particular molecule can be controlled with surface chemistry. The surface of oxidized porous Si has a point of zero charge at a pH of around 2, and so it presents a negatively charged surface to most aqueous solutions of interest. At the appropriate pH, porous $SiO_2$ spontaneously adsorbs positively charged proteins such as serum albumin, fibrinogen, protein A, immunoglobulin G (IgG), or horseradish peroxidase, concentrating them in the process. For example, a 0.125 mg/mL solution of the monoclonal antibody bevacizumab (trade name Avastin, an anti-cancer drug) spontaneously concentrates in suitably prepared porous $SiO_2$ by a factor of >100.

Porous Si can also be made hydrophobic, and hydrophobic molecules such as the steroid dexamethasone or serum albumin can be loaded into these nanostructures. Hydrophilic molecules can also be loaded into such materials with the aid of the appropriate surfactant. The native hydride surface of porous Si is hydrophobic. Such techniques have been used for short-term loading and release. Because water is excluded from these hydrophobic surfaces, aqueous degradation and leaching reactions tend to be slow. The grafting of alkanes to the surface by hydrosilylation is commonly used to prepare materials that are stable in biological media; this stability derives in large part from the ability of the hydrophobic moieties to locally exclude water or dissolved nucleophiles.

By way of example only, binding and release of: 1) Avastin (bevacizumab); 2) a DNA 16-mer; 3) IgG (using a Protein A receptor); and 4) biotinylated bovine serum albumin (using a streptavidin receptor) have been demonstrated using this methodology. The high surface area and optical interferometric means of detection lead to very high sensitivity for many of these systems, and the fact that the materials are constructed from single crystal Si substrates means they can be readily prepared using Si microfabrication technologies.

In addition to having pore characteristics (thickness, pore size, and porosity) that may be controlled by the current density, duration of the etch cycle, and etchant solution composition, the porous silicon film may also be used as a template to generate an imprint of biologically compatible or bioresorbable materials (see e.g., Li et al., Nanostructured casting of organic and bio-polymers in porous silicon templates; U.S. Patent Application Publication No. 20060236436; and Li, et al., Polymer Replicas of Photonic Porous Silicon For Sensing and Drug Delivery Applications. Science 2003, (299), 2045-2047). Both the porous silicon film and/or its imprint possess a sinusoidally varying porosity gradient, providing sharp features in the optical reflectivity spectrum that can be used to monitor the presence or absence of chemicals trapped in the pores. It has been shown that the particles (smart dust) made from the porous silicon films by mechanical grinding or by ultrasonic fracture still carry the optical reflectivity spectrum. These porous silicon particles can be oxidized to increase stability and injected into animal eyes without toxicity to the intraocular tissues since silica is a mineral needed by the body for building bones and connective tissue.

A porous film can be lifted off the silicon substrate, and can then be broken into micron-sized particles having a size conducive to intraocular injection. For example, in one embodiment, the micron-sized particles are sized and configured such that they may be injected into the eye with a 25 or 27-gauge needle. The particles act as one-dimensional photonic crystals, displaying an optical reflectivity spectrum that is determined by the waveform used in the electrochemical etch. This spectrum acts as an optical barcode that can be observed through human tissue using, for example, an inexpensive CCD spectrometer and a white light source. For the drug delivery methods and systems of the disclosure, a drug is impregnated and trapped in the pores, and the optical code may be used to report on the release rate of the drug in the vitreous. For details of sensing molecular transport in or out of the particles, or for sensing degradation of the particles, see published U.S. Pat. Nos. 6,248,539, 6,897, 965, and 6,720,177, "Porous semiconductor-based optical interferometric sensor," which are incorporated herein by reference. In this manner, the amount of drug may be quantified to determine how much remains within the particles, and whether administration of additional doses is necessary.

Figure 3A:
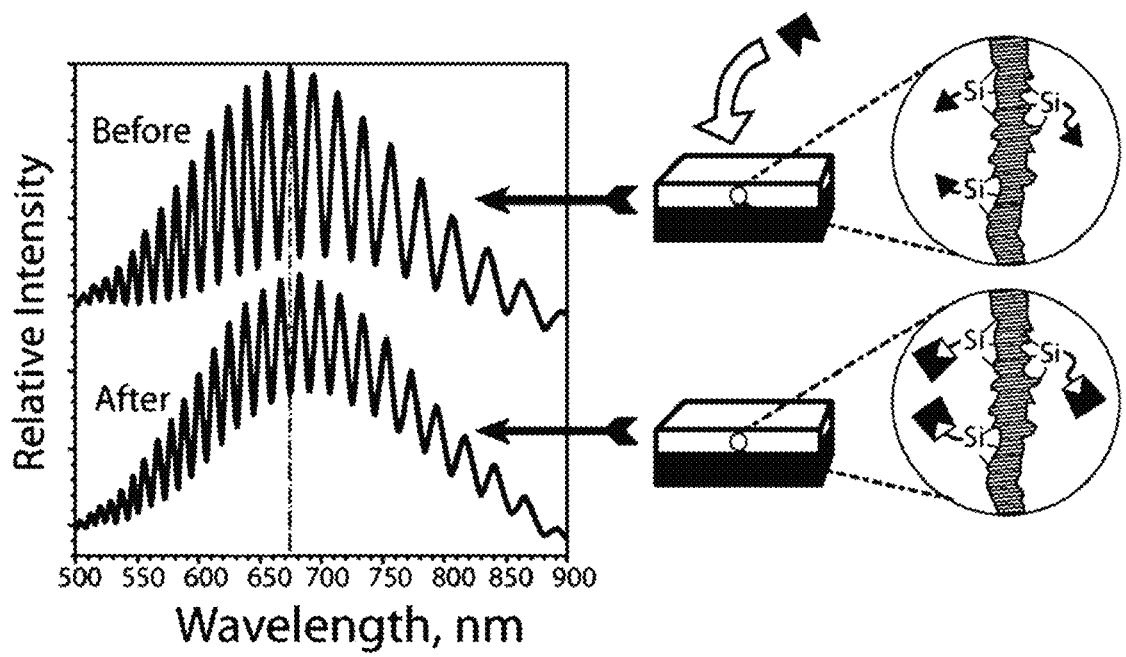
FIG. 3A-B shows representations of photo-measurements and polymer composites. (a) shows a schematic demonstrating the change in a reflectance spectrum from a single layer of porous Si upon introduction of a molecular species into the porous matrix. The change in refractive index of the composite film results in a red shift of the Fabry-Perot interference fringes. The reverse process can also be monitored, yielding a blue shift in the spectrum. (B) is a schematic diagram illustrating a templated synthesis of polymer photonic crystals using porous Si masters according to an embodiment of the disclosure.

Advantageously, the optical interference spectrum used in particle identification can be measured with inexpensive and portable instrumentation (a CCD spectrometer or a diode laser interferometer). Removal of the drug from the pores results in a change in the refractive index of the porous film and will be observed as a wavelength shift in the spectral code of the dust particle (see, e.g., FIG. 3A). Characteristic color changes are thus indicative of drug quantity remaining in the pores. Thus, the term photonic crystal is used for the—film that has been machined and sized to small crystals for intraocular injection.

A spectrometric method of detection of the oxidized "smart dust" injected into the rabbit eyes was also investigated. One eyepiece of the surgical microscope was connected to the input of a fiber-optic based spectrophotometer and this allows us to accurately focus the detecting light on the intraocular "smart dust" particles. The disclosure also provides a camera for monitoring the color change of the crystal outfitted with a spectrometer to quantitate the drug release. In yet another embodiment, a scanning laser ophthalmoscope which scans the retina and inner eye with a monochromatic light is outfitted with the appropriate wavelength to scan and detect reflectance spectrum changes allowing quantification of drug release.

In addition, to the use of porous silicon as a drug delivery composition, porous Si is an attractive candidate for use as a template because of the tunability of the porosity and average pore size. Additionally, elaborate 1, 2, and 2.5-dimensional photonic crystals are readily prepared in porous Si. Porous Si composites (e.g., porous Si and a polymer) show great promise for improving the mechanical stability and control over release rates of a delivery system. Either the composite itself or a nanostructure derived from the composite by removal of the porous Si template can be used. Porous Si combined with a biocompatible polymer can yield improved control over drug release kinetics and improved stability in aqueous media, and the use of biopolymers that are selectively cleaved by specific proteases provides the possibility of tissue-specific action.

Removal of the porous Si or porous $SiO_2$ template from a polymer or biopolymer imprint can be achieved (depending upon the polymer used) by chemical dissolution using aqueous KOH or HF, respectively, providing a free-standing porous polymer film with the optical characteristics of the master. Whether or not the process replicates the nanostructure of the master is highly dependent on the processing conditions and the type of polymer used. Also, the ability of the polymer to release from the master is dependent on the interfacial chemistry and tortuosity of the pore network.

Two synthetic approaches can be used to generate a template polymeric delivery composition or a porous Si polymer composite. In one aspect, the polymer is synthesized within the porous matrix. In another aspect, a preformed polymer is infused into the matrix by melt- or solution-casting. For drug delivery applications, it is important to use a biocompatible polymer. Any number of biocompatible polymers can be used in the methods and compositions of the disclosure as described herein. For example, hydrogels can be used. Hydrogels are commonly used in ophthalmologic devices, biosensors, biomembranes, and controlled drug delivery. Water-swollen, crosslinked polymeric networks can undergo volume phase transitions in response to environmental changes such as pH, ionic strength, temperature, or electric fields.

Figure 3B:
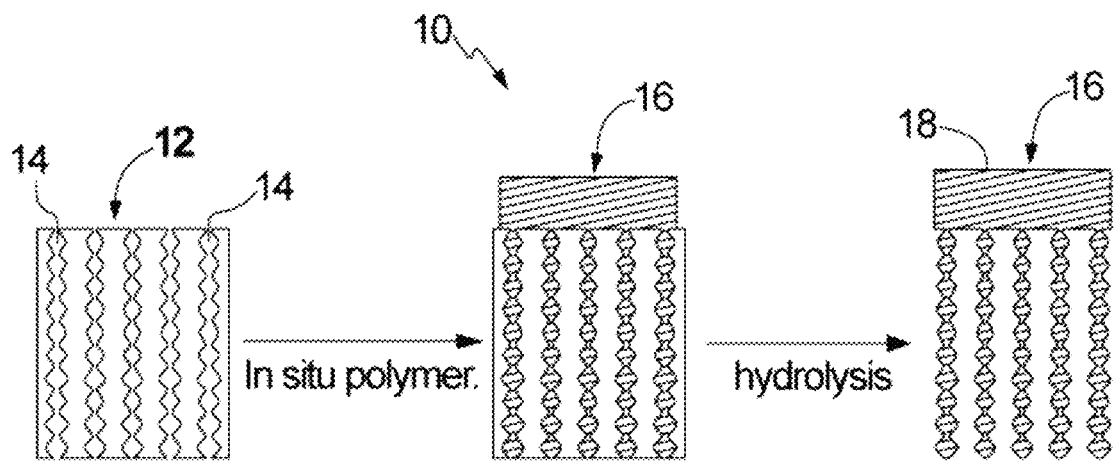
Figure 4:
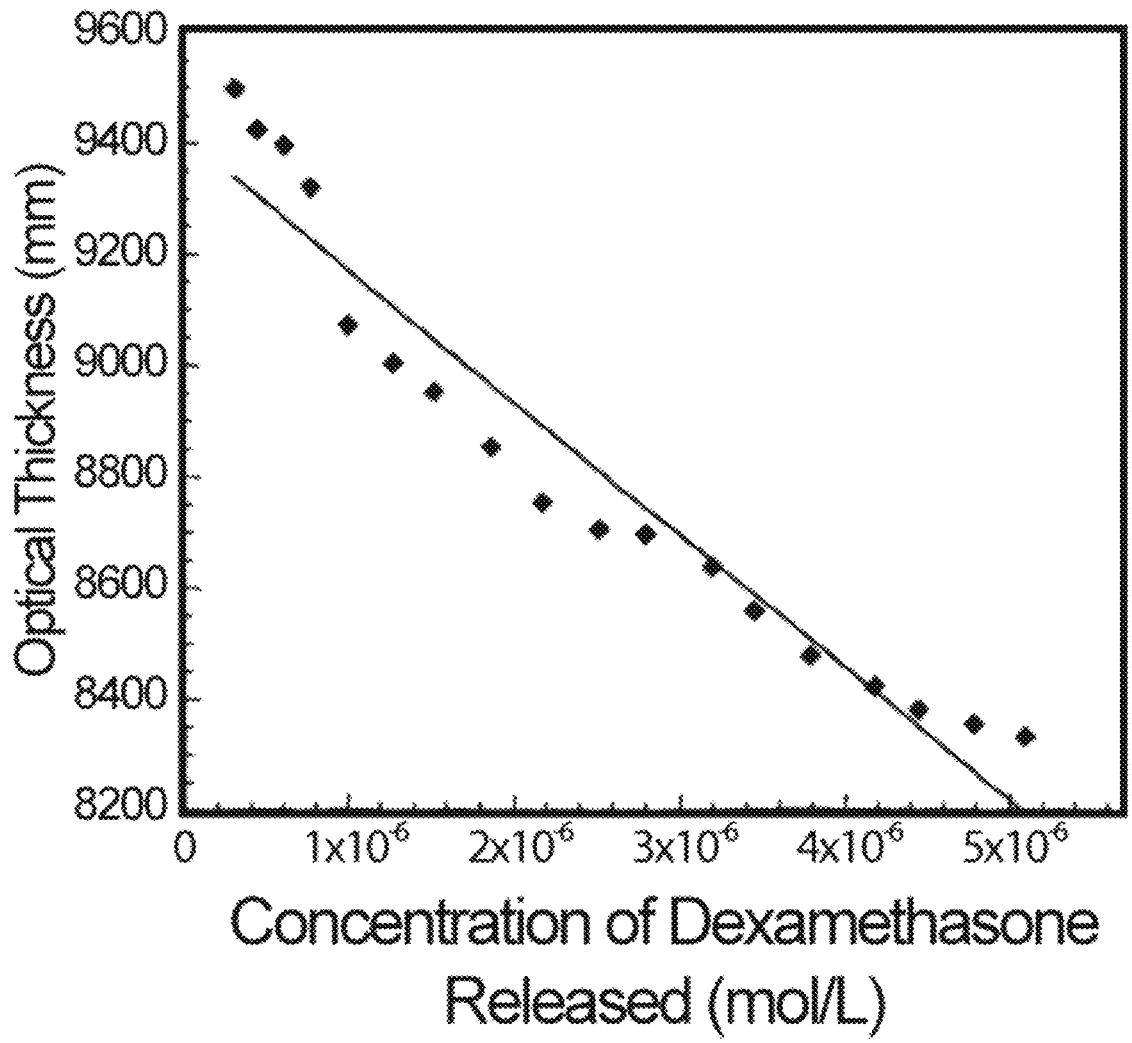
FIG. 4 is a graph illustrating a correlation between the optical thickness of an alkylated porous silicon film to the concentration of drug appearing in phosphate buffered saline solution over 2 hours.

Polymer replicas can be implanted on the sclera for trans-scleral drug release. It has been shown in rabbit eyes that polymer replicas are biocompatible and may safely and effectively remain in the eye for multiple months, if not years. Measurement of the decay in intensity of the peaks in the photonic crystal spectrum should provide a monitor of the rate of drug release from an implanted biocompatible polymer. In order to test the above hypothesis, drug-impregnated poly(L-lactide) (PL) films, cast from thermally oxidized porous silicon templates, can be prepared following a scheme, designated generally at 10, illustrated in FIG. 3. Specifically, a template (such as electropolished porous silicon), generally at 12, is provided, having pores 14 dimensioned to suit a particular application. A polymer, generally at 16, is loaded into the pores 14 to form a polymer-template composite. The template 12 is subsequently removed, leaving a polymer-based photonic film 16. Replication of the optical spectrum in the biocompatible polymer upon removal of the porous silicon template can be used to confirm the replication process. The release characteristics of the polymers can be studied.

Any number of polymeric materials can be used in the generation of a polymeric porous structure of the disclosure. Including, for example, nylon (polyamides), dacron (polyesters), polystyrene, polypropylene, polycaprolactone, polyacrylates, polyvinyl compounds (e.g., polyvinylchloride), polycarbonate (PVC), polytetrafluorethylene (PTFE, teflon), thermanox (TPX), poly(N-isopropylacrylamide), nitrocellulose, cotton, polyglycolic acid (PGA), zein, collagen (in the form of sponges, braids, or woven threads, etc.), cellulose, gelatin, poly lactic acid, poly glycolic acid, copolymers of poly lactic or poly glycolic acid, or other naturally occurring biodegradable materials or synthetic materials, including, for example, a variety of polyhydroxyalkanoates. Again, any number of polymers can work provided the polymer is transparent at the wavelengths of interest for the photonic application. If the template is to be removed, the polymer should be a solid and not a liquid. Typical polymers can include, for example, Poly dimethyl siloxane (PDMS), poly lactic acid (PLA), PLGA, polypropylene, polyethylene, polystyrene, and clear epoxy.

The degradation of the photonic structure in these films can be characterized in pH 7.4 aqueous buffer solutions, in vitro and in vivo. In accelerated degradation studies, polymer imprints impregnated with caffeine were studied. The intensity of the rugate peak displays an approximately exponential decay when the polymer is dissolved in pH 10 buffer. Simultaneous measurement of the decay of the spectral peak and the appearance of caffeine in the solution (caffeine absorption feature at 274 nm) confirmed that the drug was released on a time scale comparable to polymer degradation.

Embodiments of the disclosure also contemplate vectorial drug delivery. The polymer-based photonic film shown in FIG. 3 contains a polymer "cap" 18 on one side of the film.

Films prepared in this manner will leach drug out one side of the film, allowing greater control of the drug delivery parameters. Manufacturing variables are channel sizes and packing.

For intraocular delivery of drugs, a doctor or clinician may look through the iris of the eye and into the clear part of the eye to observe the colors of the injected particles. In this manner, the amount of drug remaining or the degree to which the particles have dissolved may be monitored, which in turns permits the doctor or clinician to forecast the length of time before the particles completely dissolve, and to predict when the patient may need subsequent injections.

Other embodiments include use of a porous silicon or silicon/polymer composite at a particular location of the eye, or using the porous silicon or silicon/polymer composite as a template to generate other biologically compatible or biologically resorbable materials for similar use. Biodegradable polymer imprints may be made from porous silicon templates, which may be used as drug delivery contact lenses or implants at an appropriate location of the eye, including the ocular surface and retrobulbar surface.

Another embodiment of the disclosure include drug(s) impregnated in porous films configured to be worn or attached on the front of the eye. A contact lens formed of impregnated porous thin film material, for example, comprises and embodiment of the disclosure. While another embodiment encompasses a contact lens, it also contemplates other similarly curved solid template correspondingly shaped with a front surface of the eye, as well as being configured to join the eye at the sclera as an episcleral plaque. The particular drug or drugs to be used with the polymer imprint may be added to the imprint solution prior to casting or engineered into the pores of the imprint after casting. Accordingly, the embodiment of the disclosure provides a system and method of drug delivery wherein porous silicon films can be variously modified to be a long-lasting intraocular drug delivery vehicle to carry various therapeutic compounds. In addition, biodegradable porous polymer imprints made from porous silicon templates can be used as a drug delivery implant to be placed at an appropriate location in the eye. The drug can be added into the imprint solution before casting or engineered into the pores after casting.

For the extraocular drug delivery, the emphasis on optical reporting declines. With the episcleral plaque, for example, delivery is retrobulbar, and it is not as easy to use an optical instrument to "read" these films. In this retrobulbar embodiment, the ability of the nanostructure to set the rate of dissolution or drug release is a property. Because the electrochemical process used to construct porous Si can control the nanostructure to such a precise degree, precise control of the dissolution and/or drug release profile of the particles or of the composites is conferred. Thus, for example, the disclosure provides a contact lens configured and arranged to cover a front extraocular surface, where a rim, or "carrier," of the contact lens would be either a silicon or silicon/polymer composite film impregnated with drug(s). The wearer would receive a sustained and monitorable release of drug through the contact lens. Another embodiment includes the use of episcleral plaques.

An episcleral plaque is an extraocular way to deliver drugs and the intraocular dust injection promotes monitoring of drug levels non-invasively. The disclosure provides use of a silicon or silicon/polymer composite film impregnated with drugs to be affixed or adhered to a retrobulbar surface of the eye. The patient would thereby receive a sustained and monitorable release of drug through the episcleral plaque.

While the disclosure provides for use with a virtually unlimited number of pharmaceutical candidates, several exemplary drugs will be discussed herein. For example, drug delivery for drugs used in treating ARMD and uveitis will be shown for purposes of illustration. These diseases require prolonged intraocular therapeutic drug levels to halt the progress of the disease and the deterioration of eyesight. However, the promising drugs for treating these diseases all share a common problem, which is the transient intraocular therapeutic level requires frequent intravitreal injections. These promising drugs include angiostatic steroids, metalloproteinase inhibitors, VEGF binding drugs, PEDF, an 8-mer peptide fragment of urokinase (uPA) and dexamethasone. These drugs may also be used to treat, for example, diabetic retinopathy. In particular, PEDF, the 8-mer peptide fragment of uPA and dexamethasone all have short intravitreal half lives.

Other drugs or "active ingredient" that can be used with the smart dust of the disclosure include any one or any combination of the following, but are not limited to, anti-angiogenic compounds such as bevacizumab, ranibizumab, pegaptanib, and other compounds in the angiogenic cascade. Also included are glucocorticosteroids such as dexamethasone, triamcinolone acetonide, fluocinolone acetonide and other comparable compounds in the corticosteroid and cortisene families. Also included are compounds such as antacids, anti-inflammatory substances, coronary dilators, cerebral dilators, peripheral vasodilators, anti-infectives, psychotropics, anti-manics, stimulants, anti-histamines, laxatives, decongestants, vitamins, gastrointestinal sedatives, anti-diarrheal preparations, anti-anginal drugs, vasodilators, anti-arrhythmics, anti-hypertensive drugs, vasoconstrictors and migraine treatments, anti-coagulants and anti-thrombotic drugs, analgesics, anti-pyretics, hypnotics, sedatives, anti-emetics, anti-nauseants, anti-convulsants, neuromuscular drugs, hyper- and hypoglycemic agents, thyroid and anti-thyroid preparations, diuretics, anti-spasmodics, uterine relaxants, mineral and nutritional additives, anti-obesity drugs, anabolic drugs, erythropoietic drugs, anti-asthmatics, bronchodilators, expectorants, cough suppressants, mucolytics, drugs affecting calcification and bone turnover and anti-uricemic drugs. Specific drugs include gastro-intestinal sedatives such as metoclopramide and propantheline bromide; antacids such as aluminum trisilicate, aluminum hydroxide, ranitidine and cimetidine; anti-inflammatory drugs such as phenylbutazone, indomethacin, naproxen, ibuprofen, flurbiprofen, diclofenac, dexamethasone, prednisone and prednisolone; coronary vasodilator drugs such as glyceryl trinitrate, isosorbide dinitrate and pentaerythritol tetranitrate; peripheral and cerebral vasodilators such as soloctidilum, vincamine, naftidrofuryl oxalate, co-dergocrine mesylate, cyclandelate, papaverine and nicotinic acid; anti-infective substances such as erythromycin stearate, cephalexin, nalidixic acid, tetracycline hydrochloride, ampicillin, flucloxacillin sodium, hexamine mandelate and hexamine hippurate; neuroleptic drugs such as flurazepam, diazepam, temazepam, amitryptyline, doxepin, lithium carbonate, lithium sulfate, chlorpromazine, thioridazine, trifluperazine, fluphenazine, piperothiazine, haloperidol, maprotiline hydrochloride, imipramine and desmethylimipramine; central nervous stimulants such as methylphenidate, ephedrine, epinephrine, isoproterenol, amphetamine sulfate and amphetamine hydrochloride; antihistamic drugs such as diphenhydramine, diphenylpyraline, chlorpheniramine and brompheniramine; anti-diarrheal drugs such as bisacodyl and magnesium hydroxide; the laxative drug, dioctyl sodium sulfosuccinate; nutritional supplements such as ascorbic acid, alpha tocopherol, thiamine and pyridoxine; anti-spasmodic drugs such as dicyclomine and diphenoxylate; drugs affecting the rhythm of the heart such as verapamil, nifedipine, diltiazem, procainamide, disopyramide, bretylium tosylate, quinidine sulfate and quinidine gluconate; drugs used in the treatment of hypertension such as propranolol hydrochloride, guanethidine monosulphate, methyldopa, oxprenolol hydrochloride, captopril and hydralazine; drugs used in the treatment of migraine such as ergotamine; drugs affecting coagulability of blood such as epsilon aminocaproic acid and protamine sulfate; analgesic drugs such as acetylsalicylic acid, acetaminophen, codeine phosphate, codeine sulfate, oxycodone, dihydrocodeine tartrate, oxycodeinone, morphine, heroin, nalbuphine, butorphanol tartrate, pentazocine hydrochloride, cyclazacine, pethidine, buprenorphine, scopolamine and mefenamic acid; anti-epileptic drugs such as phenytoin sodium and sodium valproate; neuromuscular drugs such as dantrolene sodium; substances used in the treatment of diabetes such as tolbutamide, disbenase glucagon and insulin; drugs used in the treatment of thyroid gland dysfunction such as triiodothyronine, thyroxine and propylthiouracil, diuretic drugs such as furosemide, chlorthalidone, hydrochlorthiazide, spironolactone and triamterene; the uterine relaxant drug ritodrine; appetite suppressants such as fenfluramine hydrochloride, phentermine and diethylproprion hydrochloride; anti-asthmatic and bronchodilator drugs such as aminophylline, theophylline, salbutamol, orciprenaline sulphate and terbutaline sulphate; expectorant drugs such as guaiphenesin; cough suppressants such as dextromethorphan and noscapine; mucolytic drugs such as carbocisteine; anti-septics such as cetylpyridinium chloride, tyrothricin and chlorhexidine; decongestant drugs such as phenylpropanolamine and pseudoephedrine; hypnotic drugs such as dichloralphenazone and nitrazepam; anti-nauseant drugs such as promethazine theoclate; haemopoietic drugs such as ferrous sulphate, folic acid and calcium gluconate; uricosuric drugs such as sulphinpyrazone, allopurinol and probenecid; and calcification affecting agents such as biphosphonates, e.g., etidronate, pamidronate, alendronate, residronate, teludronate, clodronate and alondronate.

Insofar as the disclosure contemplates including a virtually unlimited number of drugs, in vitro pharmacokinetic studies can be used to determine the appropriate configuration of the porous silicon film and its dust for each drug. The drug conjugated porous silicon film and its dust can be aliquoted into vitreous samples in cell culture dishes. Intensity of reflected light from the porous silicon film or its dust can be measured using a low power spectrophotometer, at the same time free drug in the vitreous sample can be measured, as a function of time for the porous film or dust immersed in the vitreous sample. Correlation between spectrophotometer change and drug concentration in vitreous can be determined and used for in vivo PK studies.

For biocompatible polymer imprints of the porous silicon film, drug can be impregnated in the polymer casting solution. Then the free standing polymer porous film can further conjugate with drug molecules to fill the pores. In vitro PK studies can be performed in a similar way as with the porous silicon film or its dust.

Optimized porous silicon smart dust adapted to the drug candidate will not be toxic after intravitreal injection and the vitreous drug half-life will be in the range of weeks to months and the drug level will sustain above the EC for months. A method includes preparing porous Si photonic crystal particles, loading the pores of those crystal particles with one or more drugs, and injecting the particles into the vitreous via syringe. The amount of drug loaded in the particles may then be monitored via one or more of a plurality of methods, such as by visual inspection, digital imaging, laser eye scan, or spectroscopic observation. Any of these four methods are non-invasive, allowing the practitioner or clinician to observe the particles through the pupil of the eye.

More particularly, one method of the disclosure proceeds as follows. Porous Si photonic crystals are formed from a porous silicon film that is electrochemically etched in a single crystal Si substrate by application of a sinusoidal current density-time waveform. The waveform varies between 15 and 45 mA/cm$^2$, with 70 repeats and a periodicity of 12.5 s. The one-dimensional photonic crystal that results has a color that depends on the waveform parameters. The conditions described above produce a film that has a strong reflectivity maximum in the green region of the spectrum. This is a convenient color for visual observation in the eye, though any color or pattern of colors (multiple spectral peaks) can be incorporated into the films. The spectral features can range in wavelength from 300 nm to 10,000 nm. The film is removed from the Si substrate using a pulse of current. Particles with dimensions in the range 1 µm to 270 µm are generated by ultrasonication.

The photonic crystals are then loaded with a drug or drugs. The pores of the photonic crystals are large enough to allow infiltration of drugs such as, for example, dexamethasone. Drug can be loaded into the film or particles by infiltration from solution. In a typical preparation, the drug loading solution comprised $6\times10^{-2}$ M dexamethasone in methanol. 25 µL of the solution was pipetted onto the porous Si film and the solvent was allowed to evaporate in air. The film was briefly rinsed with deionized water to remove any excess drug remaining on the surface that had not infiltrated the pores.

Once the drug is loaded into the pores of the photonic crystals, the photonic crystals are then injected into the patient. In another aspect, the loaded photonic crystals are oxidized to entrap the drug. The drug-loaded crystals are placed in an appropriate excipient and injected into the vitreous. After intravitreal injection, the porous silicon particles floated in the vitreous affording an ophthalmoscopically clear view of the fundus without any observed toxicity. The particles may last in the vitreous for up to four months without any noticeable abnormalities.

The optical interference spectrum used in particle identification can readily be measured with inexpensive and portable instrumentation such as a CCD spectrometer or a diode laser interferometer. Removal of the drug from the porous nanostructure results in a change in—the refractive index of the porous film and is observed as a wavelength shift in the spectrum, or a shift in the code, of the dust particle. The high surface area and optical interferometric means of detection lead to very high sensitivity for this system. Furthermore, particles can be encoded to reflect infrared light that can penetrate living tissues and enable noninvasive sensing through opaque tissue.

The described devices, systems and methods also encompass the pulsatile delivery of active ingredients, such as pharmaceutical compounds. By "pulsatile" is meant that a plurality of drug doses are released at spaced apart intervals of time. Accordingly, the devices and systems are designed, configured and manufactured to possess release profiles (e.g., release kinetics) suitable for treating specific conditions or multiple conditions. It is understood that such devices and systems can include a plurality of active ingredients each possessing a specific release profile suitable for treating multiple conditions. A pulsatile delivery system is capable of providing, for example, one or more immediate release pulses at predetermined time points after a controlled lag time or at specific sites. The system or device allows for pulsatile drug delivery, and the administration of differing sized dosages of active ingredients at different times automatically, pursuant to a pre-programmed dosage profile utilized to design, configure and manufacture a device or system provided herein. Exemplary release profiles include those that correspond to desired peaks and troughs related to disease symptoms.

Accordingly, provided herein are devices, systems and methods designed to facilitate the controlled release of an active ingredient in a biological system. In some aspects, the active ingredient is a pharmaceutical compound. The compound can be included in a suitable matrix or carrier. The matrix or carrier can further include hydrophilic binders, water-soluble diluents, surfactants, lubricants, disintegrants, antioxidants, or non water-soluble diluents, or any combination thereof.

The term "active ingredient" is intended to mean any compound having a therapeutic effect, and which is suitable for administration in a device provided herein. Active ingredients include non-peptide organic molecules, small peptides and peptide mimetics, and the like, as well as their pharmaceutically acceptable salts. The active ingredient itself may be stable upon storage or under stress conditions, but when formulated with one or more carriers it shows stability problems, e.g., it starts to degrade.

The term "carrier" is intended to mean such carriers which are commonly used in the pharmaceutical chemistry for preparing pharmaceutical formulations, see, e.g., Remington: The Science and Practice of Pharmacy, 19th Edition (1995); "Drugs and the pharmaceutical sciences", vol. 81, 1997. In particular such one or more carriers are selected from, but not limited to, hydrophilic binders, water-soluble diluents, surfactants, lubricants, disintegrants, antioxidants, non water-soluble diluents and/or other fillers known to the skilled person.

The term "pharmaceutically acceptable salt" represents salt forms of an active ingredient that are physiologically suitable for pharmaceutical use. The pharmaceutically acceptable salts can exist in conjunction with an active ingredient as acid addition primary, secondary, tertiary, or quaternary ammonium, alkali metal, or alkaline earth metal salts. Within the disclosure, the active ingredient may be prepared in the form of a salt such as pharmaceutically acceptable salts, especially acid-addition salts, including salts of organic acids and mineral acids. Examples of such salts include salts of organic acids such as formic acid, fumaric acid, acetic acid, propionic acid, glycolic acid, lactic acid, pyruvic acid, oxalic acid, succinic acid, malic acid, maleic acid, tartaric acid, citric acid, benzoic acid, salicylic acid and the like. Suitable inorganic acid-addition salts include salts of hydrochloric, hydrobromic, sulphuric and phosphoric acids and the like. The acid addition salts may be obtained as the direct products of compound synthesis. In the alternative, the free base may be dissolved in a suitable solvent containing the appropriate acid, and the salt isolated by evaporating the solvent or otherwise separating the salt and solvent.

The term "hydrophilic binder" represents binders commonly used in the formulation of pharmaceuticals, such as polyvinylpyrrolidone, copolyvidone (cross-linked polyvinylpyrrolidone), polyethylene glycol, sucrose, dextrose, corn syrup, polysaccharides (including acacia, tragacanth, guar, and alginates), gelatin, and cellulose derivatives (including hydroxypropyl methylcellulose, hydroxypropyl cellulose, and sodium carboxymethylcellulose).

The term "water-soluble diluent" represents compounds typically used in the formulation of pharmaceuticals, such as sugars (including lactose, sucrose, and dextrose), polysaccharides (including dextrates and maltodextrin), polyols (including mannitol, xylitol, and sorbitol), and cyclodextrins.

The term "non water-soluble diluent" represents compounds typically used in the formulation of pharmaceuticals, such as calcium phosphate, calcium sulfate, starches, modified starches and microcrystalline cellulose.

The term "non water-soluble diluent with non-swelling properties" represents the non water-soluble diluents as indicated above, but excluding starches and modified starches and the like.

The term "surfactant", as used herein, represents ionic and nonionic surfactants or wetting agents commonly used in the formulation of pharmaceuticals, such as ethoxylated castor oil, polyglycolyzed glycerides, acetylated monoglycerides, sorbitan fatty acid esters, poloxamers, polyoxyethylene sorbitan fatty acid esters, polyoxyethylene derivatives, monoglycerides or ethoxylated derivatives thereof, diglycerides or polyoxyethylene derivatives thereof, sodium docusate, sodium laurylsulfate, cholic acid or derivatives thereof, lecithins, alcohols and phospholipids.

The term "antioxidant" represents the three groups of antioxidants, true antioxidants, reducing agents and antoxidant synergists, such as tocopherols, tocopherolesters, alkyl gallates, butylated hydroxyanisole, butylated hydroxytoluene, ascorbic acid, citric acid, edetic acid and its salts, lecithin and tartaric acid.

The term "disintegrant" represents compounds such as starches, clays, celluloses, alginates, gums, cross-linked polymers (such as cross-linked polyvinylpyrrolidone and cross-linked sodium carboxymethylcellulose), sodium starch glycolate, low-substituted hydroxypropyl cellulose, and soy polysaccharides. Preferably, the disintegrant is a modified cellulose gum such as e.g. cross-linked sodium carboxymethylcellulose.

The drug or photonic nanocrystal of the disclosure can be formulated for in vivo delivery using the compositions and methods described above.

Although certain embodiments of the invention have been described, additional embodiments and examples are provided below. Such specific examples are not intended to limit the invention.

EXAMPLES

Porous silicon dust was injected into rabbit vitreous and no toxicity was found compared with the fellow eyes that received the same volume of phosphate-buffered saline (PBS) injection. The porous silicon film was etched using a sinusoidal current varying between 15 and 45 mA/cm$^2$, with 70 repeats and a periodicity of 12.5 s. The film was sonicated into a dust that ranged from 1 μm to 270 μm. After intravitreal injection, the porous silicon particles floated in the vitreous affording an ophthalmoscopically clear view of the fundus without any observed toxicity. The particles lasted in the vitreous for one week without any noticeable abnormalities.

Thermally oxidized silicon dust was also injected into the vitreous of four rabbits. This chemical modification of the porous silicon film was proposed as one of the alternative methods to increase the residence time of the porous silicon dust in vitreous. This approach demonstrated a great increase of the residence time of the particles in the rabbit eye compared to the previous incompletely hydrosilylated smart dust (from less than 7 days to longer than 3 weeks). In addition, by increasing the sonication time during preparation, smaller and more uniform smart dust particles were produced, which can be delivered into vitreous by the 25 or 27-gauge needle that is commonly used for intravitreal injection in the clinic.

Additional data supports use of completely hydrosilated porous Si photonic crystals that have no toxicity by clinical examination or electroretinograms or histology at 3½ months post injection, inclusive of shorter times. For example, 100 microliters of the material were injected, and the characteristic color of the crystals is seen making it clear that one can use this characteristic for monitoring drug release in the eye.

Intravitreal injection of 100 µl of oxidized porous Si photonic crystal particles in 5% dextrose was performed. The measured size of the smart dust ranged from 10 to 45 µm with an average of 30 µm; approximately 30,000 particles were injected into each rabbit eye. The injected particles appeared purplish green floating in the vitreous. From the second day some of the particles aggregated and sank onto the inferior retina. No toxicity was seen and the smart dust particles were still visible at the last examination 34 weeks later with at least half of the originally injected material remaining, as assessed by ophthalmoscopy. It is therefore anticipated that the particles would be safe and effective for at least a year if not two years. Thus, this preliminary thermal oxidation modification has greatly extended the time of intravitreal residence compared to the previous incompletely hydrosilylated smart dust. The data demonstrated that the porous silicon particle was safe as an intravitreal drug delivery vehicle. Modifications such as oxidation and silicon-carbon chain conjugation can be used to further increase the stability of the silicon dust and can make it a long-lasting slow release intravitreal drug delivery system.

A preliminary study was performed on a rat CNV model using systemic administration of an 8-mer peptide derived from urokinase plasminogen activator (uPA) to block the uPA-urokinase plasminogen activator receptor (uPAR) interaction. This 8-mer peptide was administrated subcutaneously twice daily at 200 mg/kg/d beginning at the time of induction of CNV (with laser) to introduce CNV in Brown Norway rats. Two weeks after laser treatment, simultaneous FA and ICG using scanning laser angiography was performed to identify the leaking laser burns. The results showed that this 8-mer peptide reduced the laser induced CNV by 70% compared to the control group (44.7% of laser burns leak in control group versus 13.4% in treated group, $p<0.001$). Administration of the drug intravitreally using a proposed porous silicon smart dust should maintain the desired intraocular drug level.

Thermal Oxidation of Porous Si Particles: Preliminary studies of porous Si particles oxidized and annealed at 300° C. for 2 hours in air show that the material is stable in aqueous pH 11 buffer for several days, and recent results indicate that this approach can dramatically increase the residence time of the particles in the rabbit eye. In addition, by increasing the sonication time during preparation, smaller and more uniform smart dust particles were produced which can be delivered into vitreous by the 28.5 gauge needle that is commonly used for intravitreal injection in the clinic. Intravitreal injection of 100 µl of oxidized porous Si photonic crystal particles in 5% dextrose was performed. The measured size of the smart dust ranged from 10 to 45 µm with a average of 30 µm; approximately 30,000 particles were injected into each rabbit eye. The color of the injected particles floating in the vitreous was clearly visible, which is indicative of drug release and degradation by hydrolysis. Degradation by hydrolysis is especially advantageous in that no enzymes are necessary to degrade the particles. From the second day some of the particles aggregated and sank onto the inferior retina. No toxicity was noticed and the smart dust particles were still visible until the last examination, which indicates that this preliminary thermal oxidation has more than tripled the time of intravitreal residence compared to the previous incompletely hydrosilylated smart dust. Experiments can be performed to quantify the residence time and correlate it with the chemical modification conditions such as thermal oxidation time, temperature, and ambient atmosphere.

Electrochemical Grafting of Organic Reagents: The hydride-terminated surface of p-type or p++-type porous silicon can be stabilized by electrochemical reduction of acetonitrile solutions of various organo halides. Reduction of 6-iodo-ethylhexanoate, 1-iodo-6-(trifluoroacetylamino) hexane, iodomethane, 1-bromohexane, or ethyl 4-bromobutyrate at a porous Si cathode results in removal of the halogen and attachment of the organic fragment to the porous Si surface via a Si—C bond. A two-step procedure was devised involving attachment of the functional group of interest followed by attachment of methyl groups (by reduction of iodomethane) to residual, more sterically inaccessible sites on the porous Si surface and found that electrochemical alkylation greatly improves the stability of porous Si against oxidation and corrosion in various corrosive aqueous media, and that the methyl capping procedure provides the most stable porous Si material yet reported. This chemistry also allows covalent attachment of the candidate drugs for the release studies.

Thermal Hydrosilylation of Organoalkenes: This approach provides a porous Si material that is stable even in boiling aqueous pH 10 solutions. This chemistry was extended to the dust particles and find similar levels of stability. Parameters of the reaction may be adjusted in order to identify the key parameters leading to this instability. In particular, the surface coverage (essentially the efficiency of the chemical reaction), the type of organic species grafted to the surface (alkyl carboxylates, alkyl esters, and alkyl halides), and the chain length of the alkyl species can be investigated. Reaction conditions such as the presence of added radical initiators, transition metal catalysts, and photoassisted hydrosilylation can be explored.

For each modified porous silicon film, its sonicated dust can be intravitreally injected into 3 rabbit eyes with the fellow eyes used for control. After injection, the toxicity can be monitored by slit lamp, indirect ophthalmoscope, ERG, and pathology. In addition, a remote spectrometer probe can be used to determine the clearance rate of the silica dust in vitreous on living animals through the dilated pupil. The spectrometer probe is believed to render more accurate information since the small particles may not be seen using indirect ophthalmoscope.

A spectrometric method of detection of the oxidized "smart dust" injected into the rabbit eyes was also investigated. One eyepiece of the surgical microscope was connected to the input of a fiber-optic based spectrophotometer and this allows us to accurately focus the detecting light on the intraocular "smart dust" particles. The disclosure also provides a camera for monitoring the color change of the crystal outfitted with a spectrometer to quantitate the drug release. In yet another embodiment, a scanning laser ophthalmoscope which scans the retina and inner eye with a monochromatic light is outfitted with the appropriate wavelength to scan and detect reflectance spectrum changes allowing quantification of drug release. The preliminary data showed a feasibility of this approach and the specific wavelength of a porous Si photonic film was detected with a 1 nm spectral resolution. This resolution is sufficient to determine concentration of a species such as a large protein in the porous Si film to micromolar concentration levels. As an alternative, the probe can be adapted to a fundus camera which is used for clinical retinal imaging. For the rabbit or rodent eyes, the fundus can be photographed using a fundus camera without anesthesia.

In in vitro experiments, the optical codes of the porous Si photonic crystal particles can be read using digital imaging cameras. Since the color of the particles provides an indirect measure of the amount of drug loaded, the most accurate measure is obtained using a spectrometer. However, the color resolution in a digital camera is sufficient to measure the loading to an accuracy of 10%, which is sufficient for the present application. In order to measure the degree of loading in porous Si "smart dust," the color of the particles can be recorded using a color digital camera connected to the fundus camera. Software to process the digital images and extract concentration information can be obtained with minor modifications to commercially available software. The advantage of this approach is that it requires only minor modification to existing readily available medical equipment, and it allows acquisition of data from a large number of particles simultaneously. If higher resolution concentration information is needed, the illumination light can be filtered using a monochromator or bandpass filters, providing spectral resolution equivalent to that which can be obtained with a spectrometer.

The long-lasting porous silicon film and its imprint can be further optimized for delivery of three candidate drugs (PEDF, an 8-mer peptide fragment of uPA, and dexamethasone) by controlling the pore size and morphology. These parameters are easily controlled using the appropriate anodic electrochemical etching current density, duration of the etch cycle, and etchant solution composition. Since the imprint and its porous silicon template share the similar nanostructures, it is assumed that imprints from optimized porous silicon can also be appropriate for delivering those drug candidates.

Additional in vivo data regarding the "smart dust" material after intraocular injection and new in vitro data concerning the release of dexamethasone from "smart dust" formulations is as follows. In vivo studies The new formulation of "smart dust" particles containing a silicon dioxide shell have been observed in the vitreous of living rabbits for 16 weeks and they are showing evidence of dissolution without any evidence of toxicity by slit lamp, indirect ophthalmoscopic examinations or by light or electron microscopy. More than half of the particles appear to be present at this time point indicating excellent potential as a long acting drug delivery system. Injection of "smart dust" particles containing a hydrosilylated alkyl shell into the living rabbit eye has shown no evidence of toxicity for up to five weeks of ongoing examination.

Additional in vivo studies demonstrated the increased stability of "smart dust" particles containing a hydrosilylated alkyl shell. These chemically modified particles also exhibit slower release rates for a drug. Release of dexamethasone from the modified porous silicon matrix is slowed by a factor of 20 compared to unmodified porous silicon.

Chemistries have also been developed to expand the pores in order to accommodate larger molecules within the pores, such as a modified Fab fragment of human IgG. The pore expansion procedure involves the enlargement of pores by treatment with dimethylsulfoxide (DMSO) containing hydrofluoric acid (HF). The porosity increases approximately 10% after the expansion treatment, and it was found that this chemistry allows admission of large molecules such as human IgG (150 kDa) and bovine serum albumin (67 kDa). As will be clear to artisans, the invention makes use the optical properties of porous silicon photonic crystals to monitor drug delivery rates. The shift in the reflectivity spectrum of the film coincides with release of a drug. Optical measurements were carried out while concurrent absorbance measurements were obtained as the drug-infused porous silicon films were introduced in buffered aqueous solutions. There is a linear correlation between the increase of drug concentration in solution (i.e. drug diffusing from the pores) and a change in the optical thickness of the porous silicon film.

The optical properties of porous Si have been investigated for numerous applications including chemical and biological sensors. Porous Si is a biocompatible and bioresorbable material that has also been investigated for in-vivo drug delivery and biomedical device applications. Recently, a technique to produce micro particulate photonic crystals from porous Si was developed. The distinctive particle spectrum can be observed through human tissue, (Li, Cunin et al., Science 299(5615):2045-7 (2003)) and it can be used to monitor the loading and release of various organic or biomolecules including dexamethasone, IgG and bovine serum albumin. This optical method of monitoring molecular loading and release is well suited for ophthalmic applications. The drug can be housed in the porous matrix while the optical spectrum allows non-invasive measurement of the release rate. This is the first study to characterize the intraocular properties of porous silicon particles that are capable of acting as a self-reporting drug delivery system in living animal eyes.

Figure 5:
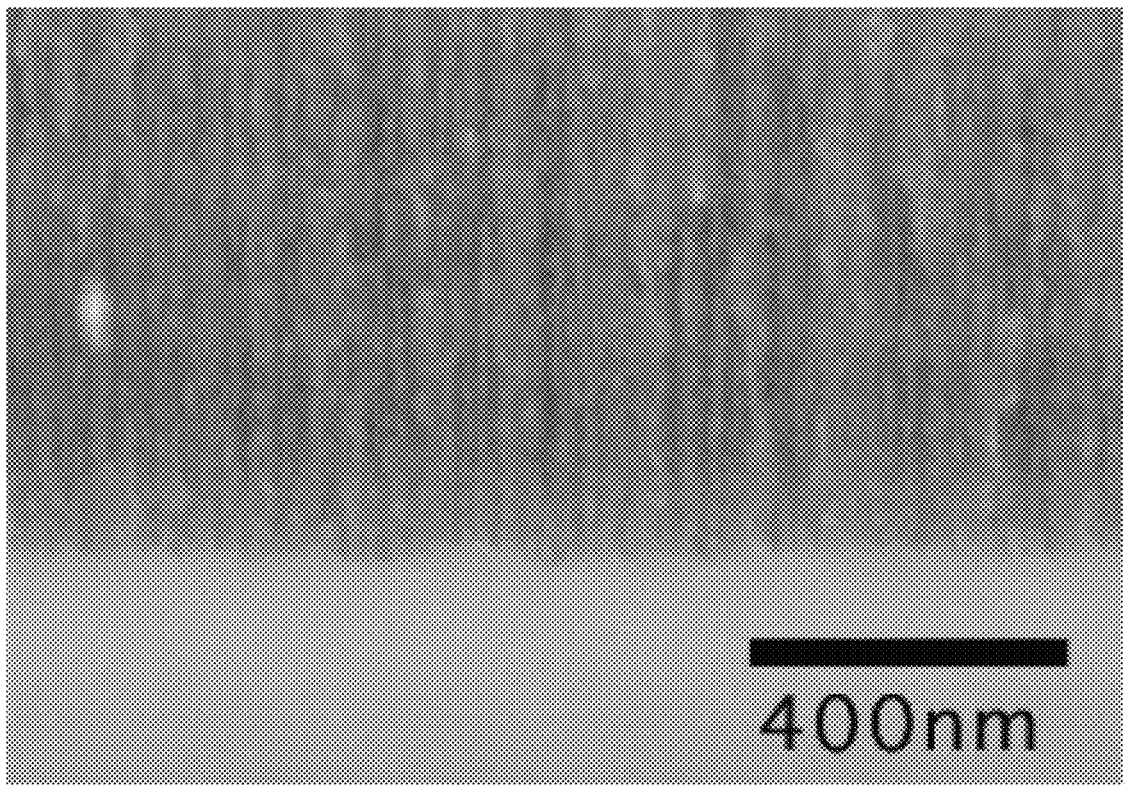
FIG. 5 shows a cross-sectional scanning electron micrograph image of an intact porous Si film prior to removal from the bulk silicon substrate and fracture into microparticles. The pores are aligned along the <100> direction of the original silicon crystal.

Fabrication of Porous Silicon Particles: Porous silicon particles were fabricated by an electrochemical etch of single-crystalline, degenerately B-doped p-type silicon (Siltronix Inc., <100> orientation, ~1 mΩ·cm resistivity) in a 48% aqueous HF: ethanol (3:1 by volume) electrolyte solution. An optical rugate structure was electrochemically etched into the Si wafer using a sinusoidal current modulation of 15-45 mA/cm$^2$, with 70 repeats and a periodicity of 12.5 seconds. The films were removed from the bulk silicon substrate by electropolishing in a 3.3% HF in ethanol solution using a current density of 200 mA/cm$^2$ for 2 min. The manufactured porous Si film was generally 20 microns thick (see FIG. 5) with a porosity of 67% as determined by gravimetric analysis. The freestanding films were then ultrasonically fractured using an ultrasonic cleaner (5 min.) to produce particles ranging in size from 1-270 microns with over 70% particles falling in the range of 15-30 microns (estimated by optical microscopy). For a 20 micron particle, there is an estimated free volume of $4 \times 10^{-9}$ cm$^3$ available for drug loading per particle, with a total free volume of $1.2 \times 10^{-4}$ cm$^3$ per particle injection in the rabbit vitreous.

Chemical Modification of Porous Si Particles: Unmodified porous silicon is known to be unstable in aqueous media because of rapid oxidation of the reactive hydride species present on the surface. In this work, two different chemical modification reactions were performed in order to stabilize the particles. The first method involves surface alkylation by means of thermal hydrosilylation with 1-dodecene, and the second method is thermal oxidation.

Surface Alkylation of Porous Si Particles: Thermal hydrosilylation was carried out on porous Si particles immediately after their preparation, following the method of Buriak (Buriak, Adv. Mater. 11(3):265-267 (2002)). The particles were placed in a Schlenk flask containing 1-dodecene and freeze-pump-thaw cycles were performed to remove oxygen. The reaction flask was filled with nitrogen and the mixture was heated at 120° C. for 2 hours. The particles were rinsed thoroughly with dichloromethane and ethanol and then dried in air. The product was characterized by FTIR, confirming the presence of alkyl species on the surface of the particles.

Thermal Oxidation of PSi Particles: Oxidation was carried out on porous Si particles immediately after their preparation. Oxidation was accomplished by heating at 80° C. in an oven in ambient air for 24 hours.

Figures 6A, 6B:
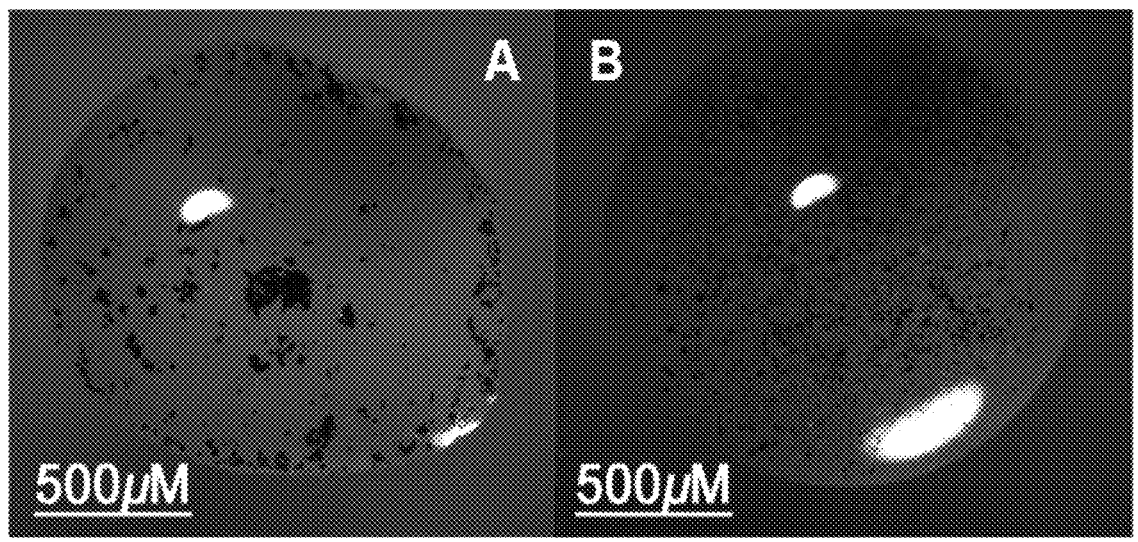
FIG. 6A-B depicts unoxidized and oxidized porous Si particles. (A) shows fresh porous Si particles in a droplet of 5% dextrose solution. Particle clumping is observed due to the hydrophobic nature of the unmodified porous Si particles. (B) shows oxidized porous Si particles in a droplet of 5% dextrose solution. These particles were observed to be more dispersed in solution, presumably because of the hydrophilic nature of the $SiO_2$ surface.

Animal studies: Eleven New Zealand Red rabbits were used to study the safety and stability of the porous silicon particles in the rabbit vitreous. All of the animal handlings were carried out in adherence to the ARVO Statement for the Use of Animals in Ophthalmic and Vision Research. Using injection methods previously published, one eye of each animal was injected with the porous Si particles, and the fellow eye was injected with the same volume of 5% dextrose to serve as the control. Three rabbits were injected with fresh (not chemically modified) porous Si particles, five rabbits were injected with hydrosilylated porous Si particles, and three were used to evaluate the oxidized porous Si particles. All of the particles were suspended in ethanol for sterilization. Prior to injection, the ethanol was evaporated and 1 mL of 5% dextrose was added to ~120 mg of the particles. One drop (~6 µL) of sample was taken for particle sizing and counting by light microscopy (FIG. 6, Panel A and Panel B). A 25 gauge needle was used to deliver 100 µL of the suspension (roughly 12 mg particles) into the rabbit vitreous through the pars plana under direct view of a surgical microscope. After intravitreal injection, the eyes were monitored with indirect ophthalmoscope, tonometer, and biomicroscopic slitlamp on day 3 and once each subsequent week thereafter. Fundus photography was carried out in the selected rabbit eyes at different intervals after injection to assess degradation of the porous Si particles. The electroretinogram (ERG) was recorded from all eyes of the animals prior to animal sacrifice. After animal sacrifice, the eye globes were enucleated for histology evaluation. The vitreous containing the hydrosilylated porous Si particles was excised from selected eyes, and the particles were examined by scanning electron microscopy.

Observation of unmodified porous Si particles in the rabbit eye: A 100 µL aliquot of porous Si particles in 5% dextrose solution was injected into the vitreous of three eyes of three rabbits using a 25 gauge needle. The particles ranged in size from 1 to 270 µm and the estimated number of particles per injection was approximately 12,000. The particles were suspended in the vitreous at the injection site (FIG. 7, Panel A) and observed to disperse into the surrounding vitreous during the following 2 to 3 days (FIG. 7, Panel B). No toxic effects were observed, and the particles degraded completely in 3 to 4 weeks (FIG. 7, Panel C). Pathologic examination by light microscopy revealed no indications of toxicity (FIG. 7, Panel D).

Observation of hydrosilylated porous Si particles in the rabbit eye: A 100 µL aliquot of hydrosilylated porous Si particles in 5% dextrose solution was injected into the vitreous of five eyes of five rabbits using a 25 gauge needle. The particles ranged in size from 1 to 300 µm (longest dimension) with an estimated 1900 particles per injection. The hydrosilylated particles became distributed throughout the vitreous within 2 to 3 days while displaying a vivid green color. Degradation was observed to be much slower than for the unmodified porous Si particles (FIG. 8). Four months after injection the animals were sacrificed, and the particles were analyzed by optical and by scanning electron microscopy. Approximately 50% of the viewable particles appeared blue-green in color (FIG. 9, Panel A). The scanning electron microscope images revealed sharp edges on the particles but a pitted surface, indicating some degree of erosion (FIG. 9, Panel B). The other three rabbits were sacrificed for histopathology. ERG examination, tonometry, and histology did not show any indications of toxicity (FIG. 9, Panel C) (see Table 1 below).

Figures 10A, 10B:
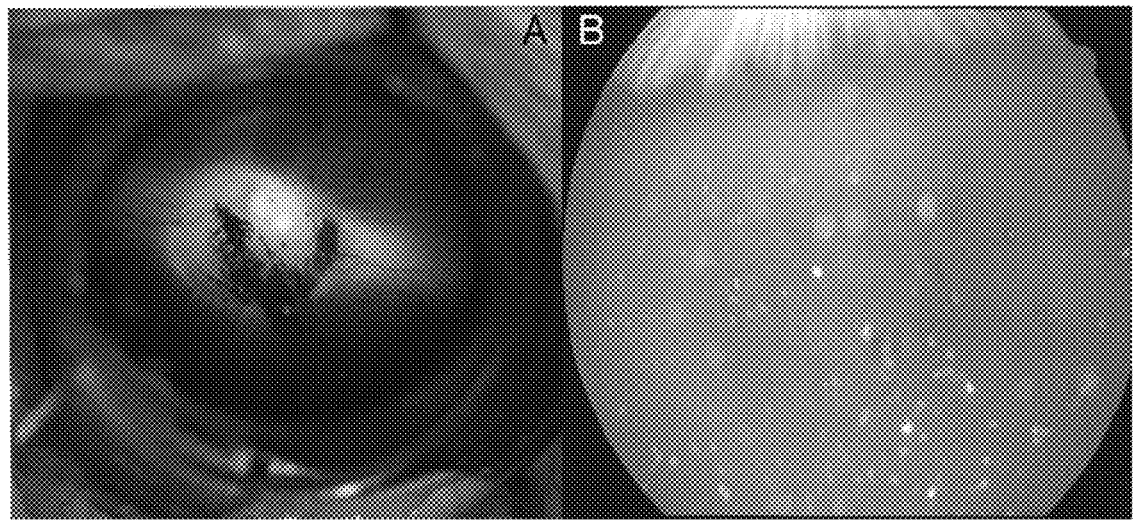
FIG. 10A-D provides images of oxidized porous Si particles following injection. (A) is a photograph taken under a surgical microscope immediately after intravitreal injection of oxidized porous Si particles. Particles can be observed suspended in the center of the vitreous above the optic nerve. (B) is a fundus photograph of a rabbit eye at 2 weeks after intravitreal injection of oxidized porous Si particles. Many violet particles and a normal fundus can be seen. The particles were initially green upon injection. The violet color indicates that significant oxidation and dissolution of the particles has occurred. Some of the particles have lost their vivid reflectance completely and appear brown in color. (C) is a fundus photograph of the same rabbit eye, 9 weeks after intravitreal injection of oxidized porous Si particles. Many of the particles have degraded and are no longer observed. The fundus appears normal. (D) is a light microscopic photograph of the retina and choroid from a rabbit eye harvested 4 months after intravitreal injection of oxidized porous Si particles. Normal chorioretinal morphology and structures are observed with a slight artificial retinal detachment. (25×, H&E staining).
Figures 10C, 10D:
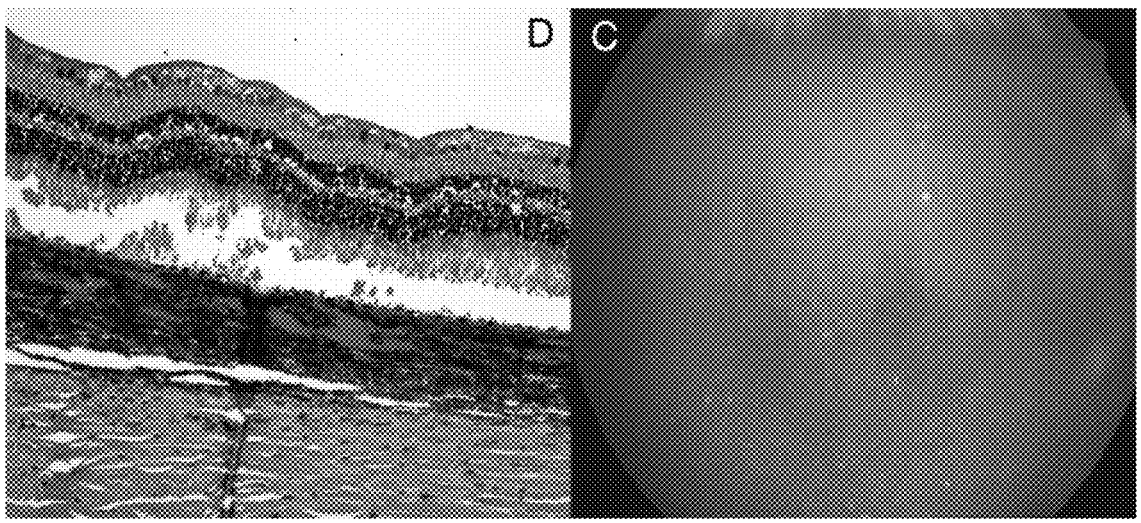
Figure 11:
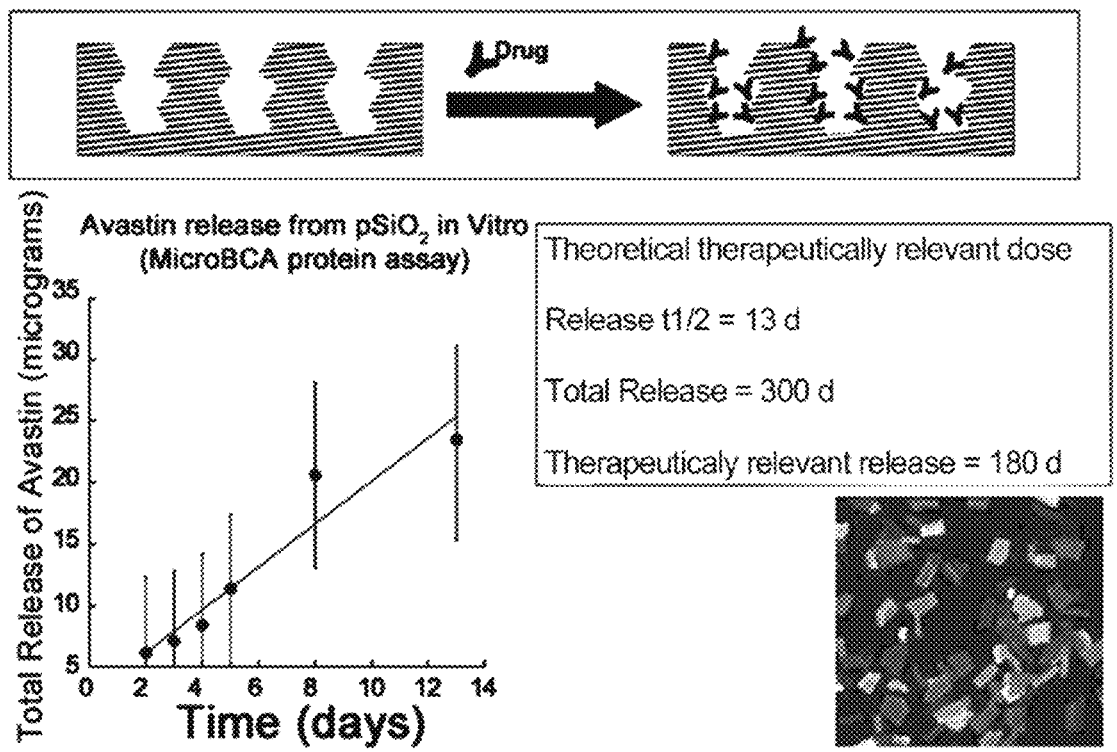
FIG. 11 provides data related to the release of bevacizumab (Avastin) from $SiO_2$ particles.
Figure 12:
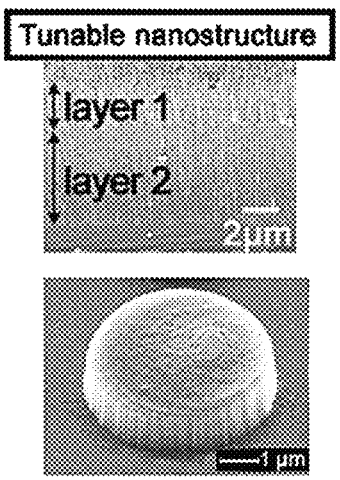
FIG. 12 provides data related to the unique features of the porous Si microparticles provided herein. Such features include spectral encoding for self-reporting capability and tunable nanostuctures for controlling release rate and for accommodating various payloads.
Figure 12:
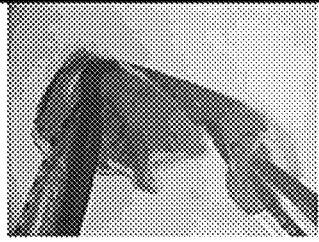
Figure 12:

Observation of oxidized porous silicon particles in the rabbit eye: A 100 µL aliquot of oxidized porous Si particles in 5% dextrose solution was injected into the vitreous of three eyes of three rabbits using a 25 gauge needle. The particles ranged from 10 to 40 µm and an estimated 30,000 particles were injected. The oxidized particles showed similar dispersion in the vitreous as the unmodified and the hydrosilylated particles. Faster degradation rates were observed for the oxidized particles than for the hydrosilylated particles (see Table 1 below). Two weeks after injection, 20% of the particles showed evidence of degradation and roughly 80% of them were reflecting purple light (FIG. 10, Panel B). Nine weeks after injection, over 80% of the observable particles lost their vivid reflective property and appeared degraded and brown. The particles had settled into the inferior vitreous or retina (FIG. 10, Panel C). The ERG, tonometry, and histology did not reveal any indications of toxicity (FIG. 10, Panel D) (see Table 1 below):

TABLE 1

Characterization of the different porous Si particle types used in intravitreal injection

| Particle type | Number of eyes tested | Maximum vitreous residence time | Estimated vitreous half-life by ophthalmoscopy | Intraocular pressure | Bio-microscopy & Indirect ophthalmolscopy | ERG | Pathology |
|---|---|---|---|---|---|---|---|
| Unmodified (Fresh) | 3 | 4 weeks | 1 week | 18.7 ± 4 (at week 4) | Normal | Normal | Normal |
| 5% dextrose | 3 | NA | NA | 15.7 ± 2 (at week 4) | Normal | Normal | Normal |
| Hydrosilylated | 5 | >17 weeks | 16 weeks | 18.2 ± 2 (at 17 weeks) | Normal | Normal | Normal |
| 5% dextrose | 5 | NA | NA | 19 ± 2 (at 17 weeks) | Normal | Normal | Normal |
| Oxidized | 3 | 12 to 16 weeks | 5 weeks | 16.7 ± 5 (at week 4) | Normal | Normal | Normal |
| 5% dextrose | 3 | NA | NA | 20 ± 4 (at week 4) | Normal | Normal | Normal |

The present studies demonstrate that porous Si particles can be safely injected into rabbit vitreous, and the unmodified particles degrade in three to four weeks without evidence of toxicity. Chemical modification of the particle and pore surface, either by grafting of dodecyl species (hydrosilylation) or by conversion to $SiO_2$ (thermal oxidation) dramatically increases the stability and vitreous residence time of the particles. This indicates that hydrosilylated or oxidized porous Si particles may be used as a long-lasting intravitreal drug delivery vehicle. Furthermore, by controlling the extent of oxidation or hydrosilylation, the vitreous residence time of the particles may be manipulated to fit the specific treatment modality.

Porous Si has been studied previously in physiological aqueous solutions and was found to dissolve into the form of orthosilicic acid, which is vital for normal bone and connective tissue homeostasis. (Anderson, Elliott et al. 2003) However, porous Si dissolution has never been studied in vitreous, which is a complex biological solution with constant fluid turn over. This type of condition is not easily duplicated in an in vitro setting. Therefore, the dissolution and the associated potential toxicity must be studied directly in the living eyes.

The unique photonic properties of porous Si make this material ideal for drug delivery by imparting a potential self-reporting feature within the delivery system. The wavelength of the spectral peak reflected from porous Si photonic crystals is dependent on the refractive index (n) of the porous Si matrix (Link and Sailor 2003). Changes in refractive index of the porous Si layer occurs as aqueous solution (n=1.34) replaces organic molecules or proteins (n~1.4) in the pores results in a blue shift of the reflectivity peak, producing an observable color change. A spectral blue shift is also expected as the Si matrix (n~3.5) is oxidized to $SiO_2$ (n~1.7) or as the $SiO_2$ matrix dissolves. In the present case, the initial green color of the photonic crystals is observed to turn blue or violet after several days to weeks in vitreous (depending on the surface chemistry) indicating dissolution of the porous matrix. After extended periods in vitreous, some of the particles lose their vivid reflectance and appear brown in color. The brown color is attributed to light absorption by residual Si in a particle whose photonic signature has shifted into the ultraviolet range. It is also possible that the signature spectrum of the photonic crystal no longer exists due to extensive degradation of the periodic nanostructure. This unique signature spectrum of the photonic crystal could be utilized to monitor drug release through the transparent optical medium of the eye using a simple CCD spectrometer device that would provide a non-invasive method to monitor drug release. This would be an advantage over other drug delivery materials such as biodegradable and bioerodible polymeric microparticles.

The fact that certain preparations of the porous Si particles have long vitreous lifetimes and display no apparent toxicity indicates that porous Si may be used as an intravitreal delivery material. With the advent of many intravitreal injectable therapeutics, such as dexamethasone, pegaptnib (Macugen), bevacizumab (Avastin), and the recently FDA-approved ranibizumab (Lucentis), repeated intravitreal injections can potentially generate serious problems. These procedures impose life quality issues with patients and raise the risk of intraocular infections. Trapping such compositions in porous Si microparticles by an encapsulant or by covalent or electrostatic interactions between the drug and the porous Si particles, allows for the composition to be slowly released as the particles degrade. This would eliminate the necessity of frequent injections.

A 100 µl intravitreal injection as used in the present rabbit studies typically contains ~30,000 porous Si particles, each approximately 50 microns square and 20 microns thick. It was calculated that at least ~50 mg of dexamethasone per gram of porous Si material can be loaded. Assuming that the porous Si particles display first order dissolution kinetics and that drug release occurs concomitant with particle dissolution, then the steady-state concentration of drug in the eye can be approximated using the dissolution mechanisms of Dove and Crerar (Geochimica Et Cosmochimica Acta 69(21):4963-4970 (2005)). With this model, the dissolution of the porous Si particles can be approximated by this overall reaction:

$$SiO_2 + 2H_2O = H_4SiO_4$$

Where the species $H_4SiO_4$ represents the water-soluble form of silicic acid. The rate expression for this reaction is dependent on the total surface area of the particles exposed to solution and the mass flow rate of silicic acid out of the system. For the particulate system, the appearance of silicic acid in solution was assumed to correlate with the appearance of drug in solution, and that the total surface area of particles exposed to solution is proportional to the number of particles, N. As the particles dissolve, the drug would be released, and the steady-state concentration of drug in the eye can be calculated based on the following relationship that has been adapted from Dove's model:

$$M_d = [t_{1/2}(\text{drug})/t_{1/2}(\text{particle})] \times N \times L$$

Where $M_d$ is the mass of free drug in the vitreous, N is the number of particles injected per eye, L is the mass of drug loaded per particle, and $t_{1/2}$ (drug) is the half-life of free drug in vitreous, and $t_{1/2}$ (particle) is the half-life of the particles in vitreous.

In general the longer the particle half-life, as demonstrated for the hydrosilylated particles and oxidized particles, the lower the steady-state concentration of drug. For particles with a 60-day half-life and an initial loaded drug mass of 600 µg in 12 mg of PSi particles (~30,000 particles), the steady-state concentration of dexamethasone with a vitreous half-life of 3.48 h would be 1 µg/mL in rabbit vitreous (1.4 ml), which is above the therapeutically relevant dose of >5 ng/mL. The particles may deliver a drug at therapeutically relevant quantities for at least 3 half-lives of the particles (180 days).

Drugs with a longer vitreous half-life such as Avastin (5 days) should be able to further extend the period between injections. For Avastin, a loading capacity of about 1-10, 10-20, 20-50, 50-100, or 100-500 mg of drug per gram of particles may be suitable for treating conditions responsive to the drug. In one example, the initial amount of drug in a 0.1 cc injection of porous Si loaded with Avastin may be approximately 100 µg of drug. If the half-life of the particles is 60 days, then the steady-state concentration of drug in vitreous would be ~8 µg/mL. The therapeutically relevant dose of Avastin as an intraocular treatment is generally considered >22 ng/mL. It is understood that the skilled artisan can readily determine the loading capacity of the particles provided herein based upon various factors, including the type of active ingredient to be associated with the particles. It is also understood that the dosage of an active ingredient associated with treating a particular disorder can be modified according to various methods known to the skilled artisan.

The disclosure demonstrates the intravitreal biocompatibility of porous Si microparticles and the feasibility of porous Si as a platform for an intraocular drug delivery system. As noted herein, fresh porous Si particles (3 eyes), oxidized porous Si (porous $SiO_2$) particles (3 eyes), and hydrosilylated porous Si particles (5 eyes) were tested in rabbit eyes. No toxicity was found by using slitlamp to monitor the anterior segment, or by using indirect ophthalmoscope to monitor posterior segment. The lack of toxicity was also confirmed by eletroretinography and histology by light microscopy. The hydrosilylated and oxidized particles were observable in the vitreous until the end of the 4 month study.

The current study also demonstrates that the Si materials are typically converted into particulate form by ultrasonication. By extending the sonication time, a more evenly distributed and smaller particles (mean size of 20 μm) can be produced and they are more compatible with the intravitreal injection method. Further, the two chemical modifications made to the porous Si materials (oxidation and hydrosilylation) led to dramatically increased intravitreal stability and slower degradation. The estimated vitreous half-life increased from one week (fresh particles) to five weeks (oxidized particles) and to 16 weeks (hydrosilylated particles).

Also provided herein are novel methods for producing porous $SiO_2$ particles by oxidation of porous Si at 800° C. Particles manufactured in this manner are more hydrophilic than the previous oxidized ones which were processed at 220° C. This new type of porous $SiO_2$ was injected into 6 rabbit eyes and no toxicity (including ERG) was observed during the 5 month ongoing study. This new type of porous $SiO_2$ allowed more efficient loading of the IgG-based drug Avastin, a candidate drug for treatment of macular degeneration.

The porous $SiO_2$ particles oxidized at 800° C. were loaded with Avastin and 100 μl of particles (containing 225 μg avastin) were injected into 3 rabbit eyes. 20 weeks after injection, the vitreous Avastin level was still 50 ng/ml which is higher than the $IC_{50}$ of Avastin (22 ng/ml).

A porous Si-polymer composite plaque was prepared and surgically implanted on the rabbit eye globe under conjunctiva and Tenon. These plaques have the same optical feature and nano pore structure as their porous Si film templates and the nano pores open to only one side of the plaque, allowing unidirectional drug release. These plaques are well tolerated by the rabbit eyes. Accordingly, the compositions and methods provided herein achieve slow release and long lasting drug delivery to treat macular degeneration, diabetic macular edema, choroidal neovascularization and retinal vein occlusion and uveitis etc vitreoretinal diseases.

These embodiments are meant to be illustrative examples and not exhaustive of the types of useful drug delivery structures that can be manufactured using the materials and methods described herein. The structures and methods discussed above will have great utility for a variety of applications including, but not limited to, controlled, sustained and programmable drug delivery.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the spirit and scope of the appended claims.

What is claimed is:

1. A composition comprising:
   a porous particulate material comprising silicon dioxide, the porous particulate material having been heated in an oxidizing environment at a temperature at or above 800° C.; and
   a drug or biologically active material within the porous particulate material.

2. The composition of claim 1, wherein the porous particulate material is a microscopic porous particulate material.

3. The composition of claim 1, wherein the porous particulate material displays a particle size of between about 0.1 μm and 100 μm.

4. The composition of claim 1, wherein the porous particulate material displays a particle size of between about 1 μm and 100 μm.

5. The composition of claim 1, wherein the porous particulate material displays a porosity of between about 40% and 80%.

6. The composition of claim 1, wherein the porous particulate material displays a layered nanostructure.

7. The composition of claim 1, wherein the porous particulate material further comprises a polymeric material.

8. The composition of claim 1, wherein the drug or biologically active material is selected from the group consisting of: an angiostatic steroid, a metalloproteinase inhibitor, a VEGF binding drug, a pigment epithelium derived factor, an 8-mer peptide fragment of urokinase, a modified RNA, a modified DNA, a fragment derived from an immunoglobulin, and dexamethasone.

9. The composition of claim 1, wherein the drug or biologically active material is bevacizumab, ranibizumab, or pegaptanib.

10. The composition of claim 1, wherein the pores are selectively dimensioned to obtain a desired reflective wavelength.

11. A pharmaceutical composition comprising the composition of claim 1 and a pharmaceutically acceptable carrier.

* * * * *